(12) United States Patent
Chandrasekaran et al.

(10) Patent No.: US 6,210,408 B1
(45) Date of Patent: Apr. 3, 2001

(54) GUIDE WIRE SYSTEM FOR RF RECANALIZATION OF VASCULAR BLOCKAGES

(75) Inventors: Verivada Chandrasekaran, Mercer Island; Zihong Guo, Bellevue, both of WA (US); Brooke Qin Ren, Champlin; Byron Fedie, Coon Rapids, both of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/256,977

(22) Filed: Feb. 24, 1999

(51) Int. Cl.[7] .................................................. A61B 18/18
(52) U.S. Cl. ........................... 606/41; 606/194; 600/585; 607/122
(58) Field of Search .................................. 606/41, 45, 39, 606/34, 159, 170, 180, 194; 607/101, 119, 122; 600/585

(56) References Cited

U.S. PATENT DOCUMENTS

| | | | |
|---|---|---|---|
| 4,762,130 | 8/1988 | Fogarty et al. | 128/348 |
| 5,019,042 | 5/1991 | Sahota | 604/101 |
| 5,179,961 | 1/1993 | Littleford | 128/772 |
| 5,300,068 | 4/1994 | Rosar et al. | 606/34 |
| 5,320,605 | 6/1994 | Sahota | 604/101 |
| 5,364,393 | 11/1994 | Auth et al. | 606/34 |
| 5,501,227 | 3/1996 | Yock | 128/662.06 |
| 5,540,659 | 7/1996 | Teirstein | 604/104 |
| 5,626,576 | 5/1997 | Janssen | 606/41 |
| 5,797,948 | 8/1998 | Dunham | 606/194 |

FOREIGN PATENT DOCUMENTS

| | | | |
|---|---|---|---|
| 0 688 580 A1 | 6/1994 | (EP) | A61N/5/10 |
| 0 633 041 | 1/1995 | (EP) . | |
| 0 688 580 | 12/1995 | (EP) . | |
| 0 810 004 | 12/1997 | (EP) . | |
| WO 97/18768 | 5/1997 | (WO) . | |
| WO 99 42162 | 8/1999 | (WO) . | |

OTHER PUBLICATIONS

H.M. Jones and E.E. Kunhardt, "The Influence of Pressure and Conductivity on the Pulsed Breakdown of Water," *IEEE Transactions on Dielectrics and Electrical Insulation*, vol. 1, No. 6, Dec. 1994, pp. 1016–1025.

*Primary Examiner*—Linda C. M. Dvorak
*Assistant Examiner*—David M. Ruddy
(74) *Attorney, Agent, or Firm*—Lyon & Lyon LLP

(57) ABSTRACT

A system for recanalizing an occluded blood vessel including a centering catheter employed to center an ablative guide wire within the blood vessel as the guide wire traverses the occlusion. The centering catheter includes a catheter body with an operative lumen through which the ablative guide wire is slidingly disposed. The centering catheter further includes a distally disposed centering mechanism that, when activated, centers the ablative guide wire within the blood vessel as it traverses the occlusion. The centering mechanism can comprise various embodiments including a single inflatable balloon or segmented inflatable balloon, which is in fluid communication with an inflation lumen. An airless preparation lumen may be disposed within the inflation lumen for ease of centering catheter preparation. The ablative guide wire includes insulation that is preferably formed of heat shrink tubing, which is stretched prior or concurrently with the heating process. The ablative guide wire includes a distal ablation tip having a non-traumatic structure and at least one discontinuous feature for creating high current densities for more efficient tissue ablation.

7 Claims, 25 Drawing Sheets

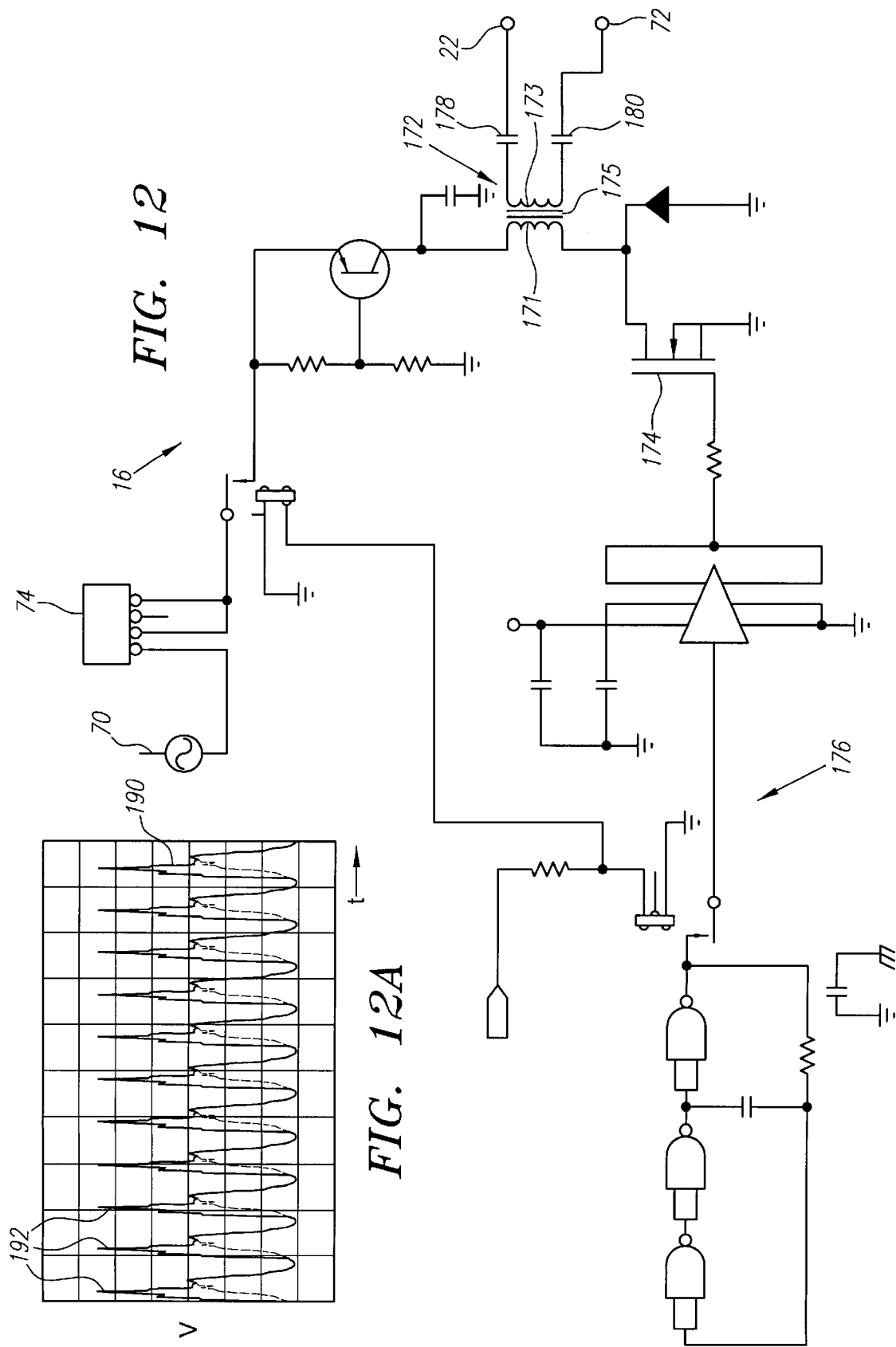

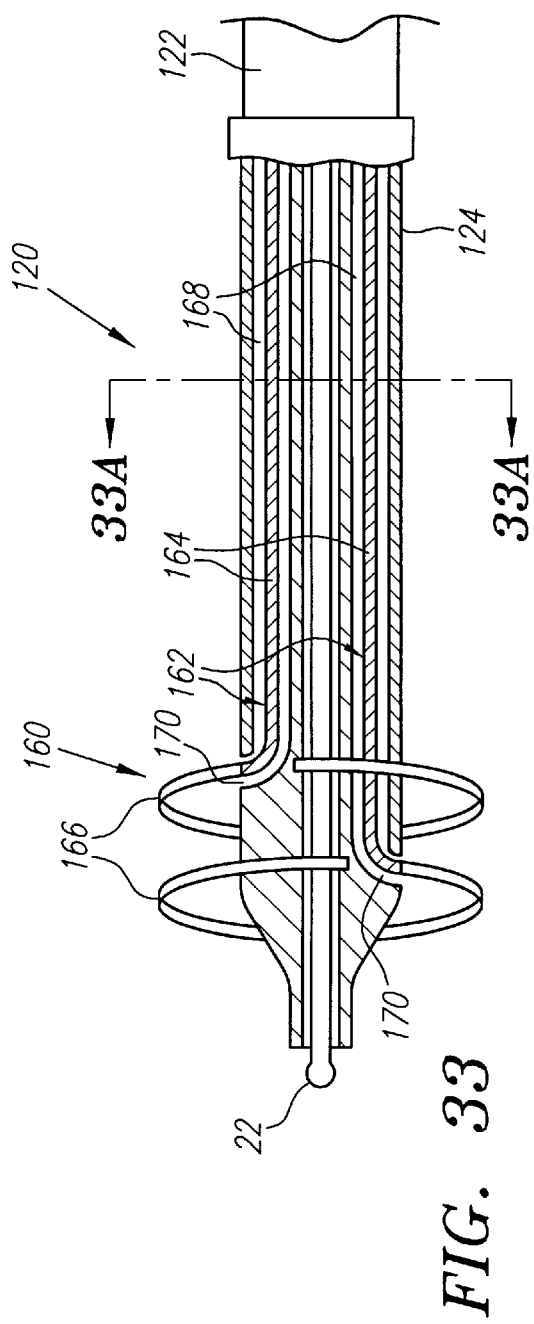
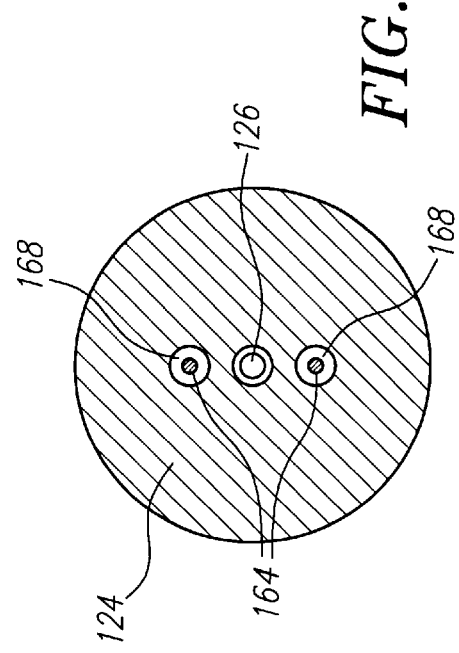

GUIDE WIRE SYSTEM FOR RF RECANALIZATION OF VASCULAR BLOCKAGES

FIELD OF THE INVENTION

The present invention is directed to methods and apparatus for recanalizing occlusions, i.e., atherosclerotic plaque build-up, in blood vessels, thereby permitting access to the occlusion by apparatus for resolving and removing the occlusion in the blood vessel in order to improve blood flow therein.

BACKGROUND

The single largest cause of cardiovascular disease is sclerosis ——a build-up of fatty or calcific deposits in the arterial lumen. These deposits can impair, and in severe cases, totally obstruct, i.e., become an occlusion, the flow of blood through the artery. A number of medical devices have been designed to displace, disperse or extract the occlusive deposits. Most of these devices operate over or in conjunction with a guide wire used to navigate the vasculature and traverse the occlusion location. The initial placement of the guide wire can be problematic in cases of total or near-total occlusion. Known techniques for traversing a total occlusion involve forcibly advancing a blunt catheter through the occlusive material (the Dotter technique), or using rotational means (orthogonal displacement of friction).

A more recent development involves using an RF-activated guide wire to electrosurgically recanalize the occlusive material, the details of which are described in U.S. Pat. No. 5,364,393 issued to Auth et al., which is fully incorporated herein by reference for all that it discloses and teaches. As taught in Auth, an electrically conductive guide wire is proximally connected to a radio frequency (RF) generator, which when operated transmits RF energy through the guide wire to a spherical ablation tip.

More particularly, the guide wire is first advanced through the vasculature of a patient, via a guiding catheter or guide sheath, until it reaches the occlusive material. With the spherical ablation tip in contact with the occlusive material, the RF generator is operated and the guide wire tip is advanced through the occlusive material. A therapeutic device used to treat the occlusive disorder is then advanced over the guide wire in accordance with known techniques.

Although the recanalization technique taught by Auth is generally effective, it is desirable to improve the devices and methods used in this approach to provide a more efficient and safe treatment of sclerosis caused by total or near-total occlusions within the arterial vasculature.

In particular, to remove or ablate the occlusive tissue matter quickly and effectively, the electrode tip of the ablative guide wire must be supplied with a potential high enough to ionize or break down the liquid contained in the tissue. This is known as a "spark erosion" process. With a monopolar guide wire electrode tip used in conjunction with a dispersive electrode or ground pad located on an external portion of the patient's body, an ionizing arc from the electrode tip is used to instantaneously convert the occlusive matter into a plasma state, in effect, vaporizing the tissue into particulate matter that is safely absorbed by the blood stream. Once the spark erosion process is initiated, a lower energy potential may be employed to maintain the plasma conversion as the guide wire tip is moved through the occlusive matter.

Towards this end, the RF generator system must provide the guide wire electrode tip with sufficient voltage or potential to initiate the spark erosion process. Typical RF generators, such as those used in electrosurgery or electrophysiology, are capable of generating a high potential, but deliver a constant output level under all load impedance conditions. Within the body, however, the load impedance seen by the guide wire electrode tip may vary greatly, depending upon the relative liquid content of the body tissue it contacts, i.e., the lower the liquid content, the higher the impedance. For example, blood impedance will typically range from 150 to 200 ohm/cm. Healthy vessel wall impedance will typically range from 300 to 400 ohm/cm. Occlusive tissue impedance, on the other hand, depending on the degree of calcification, will normally exceed 600 ohm/cm, ranging from 1000 ohm/cm to as high as 3000 ohm/cm.

Because it is difficult to determine the exact position of the guide wire electrode tip within an occluded vessel, producing a sufficiently high potential to initiate the spark erosion process can be problematic. In particular, when in contact with relatively low impedance blood or healthy vessel wall tissue, a sufficient potential is difficult to achieve without increasing the output power to a level that may cause damage to tissue remote from the surgical site, e.g., in the form of unwanted charring or ablation of healthy tissue. The increased power may also pose risk of a dangerous electrical shock to the attending surgeon, as well as loss of control sensitivity.

U.S. Pat. No. 5,300,068("Rosar") discloses an RF generator system for selectively providing a train of modulated electrical energy pulses in a modulated continuous wave signal (preferably a cosine squared wave shape) to an electrosurgical electrode disposed on a guide wire, wherein the output impedance of the source of the pulses is continually matched to the load impedance seen by the electrode. In particular, the Rosar generator system measures the relative electrical energy produced by an arc in response to a given electrical pulse, and compares the relative electrical energy to a predetermined value to determine an energy difference. The energy level of a subsequent pulse is then adjusted to reduce the measured difference towards a pre-selected value. According to the Rosar patent, this automatic impedance matching compensates for the changing impedance conditions at the electrode, to ensure an efficient power transfer takes place. In particular, maximum power transfer will occur if the output impedance at the electrode tip is substantially equal to the load impedance of the body tissue (or blood) in contact with the electrode tip.

However, the Rosar generator system is relatively complex and, thus, expensive to implement. Further, because the ablation electrode power output is maximized over all impedance levels, overheating of the electrode in the blood pool or when in contact with healthy vessel wall tissue may result, thus damaging the electrode structure and potentially harming the patient.

Thus, it would be desirable to provide a simplified RF generator system for providing energy pulses to the electrode tip of an ablation guide wire of a voltage potential sufficient to initiate the spark erosion process when in contact with relatively high impedance occlusive tissue, but which will minimize power output when in contact with relatively low impedance blood or healthy vessel wall tissue.

SUMMARY OF THE INVENTION

The present invention is directed to improved catheter devices and methods for recanalization of an occluded blood vessel within the vasculature of a patient.

In accordance with one aspect of the invention, centering mechanisms are provided for properly positioning an ablative guide wire tip within an occluded blood vessel for performing a recanalization of the blood vessel.

In a preferred embodiment, a centering catheter for positioning a guide wire in a blood vessel is provided. The centering catheter includes an elongate catheter body having a distal end and an operative lumen. The lumen has a distal end opening, such that a guide wire disposed in the lumen may be advanced beyond the distal end opening. A centering mechanism operable to secure the distal end of the catheter body within a blood vessel is mounted proximate the distal end of the catheter, such that a distal guide wire tip is positioned in the lumen proximate the distal end opening within the blood vessel. It is preferred that the centering mechanism be capable of positioning the guide wire tip both axially and longitudinally within the vessel lumen.

In preferred embodiments, the centering mechanism may be variously constructed to optimize the centering of the guide wire ablation tip depending on the blood vessel geometry at the location of the occlusion. By way of non-limiting examples, in a preferred embodiment best suited for occlusions located in a rectilinear region of a blood vessel, a segmented, inflatable balloon is employed as the centering mechanism. In another preferred embodiment, the centering mechanism comprises a resilient support structure disposed within the catheter body proximal to an inflatable balloon. The resilient support is pre-shaped into a selected complex geometry, such as, e.g., a helix or a bi-planar wave, to best conform the catheter body to wall of the blood vessel. Preferably, the resilient support is composed of a shape memory material, such as, e.g., Nitinol.

A preferred method for recanalization of a blood vessel employing a guide wire centering mechanism includes:
positioning a conductive guide wire having a distal end ablation tip into a blood vessel, such that the ablation tip is adjacent an occlusion to be traversed;
centering the guide wire ablation tip within the blood vessel;
conveying radio frequency (RF) RF energy through the guide wire to the distal ablation tip; and
advancing the energized ablation tip through the occlusion.

In accordance with a further aspect of the invention, a catheter for use as, e.g., a centering catheter is provided wherein air trapped in a distal end inflatable body may be readily purged. In a preferred embodiment, the catheter includes an elongate catheter body having proximal and distal ends. An inflatable body defining an interior region is mounted to the catheter body proximate the distal end of the catheter body. A first lumen extends through the catheter body and has a distal opening in communication with the interior region. A second lumen is disposed (e.g., concentrically) within the first lumen and also has a distal opening in communication with the interior region.

To purge air trapped in the inflatable body, a pressurized fluid medium is introduced through the first lumen into the interior region, forcing the air back out through the second lumen. Preferably, the first and second lumens terminate at opposite ends of the interior region, so that substantially all of the trapped air is pushed out of the interior region.

In accordance with yet another aspect of the invention, methods for manufacturing an insulated, conductive guide wire for use in intravascular medical procedures are provided. A preferred method includes:
placing an insulation tubing over at least a portion of an electrically conductive wire;
stretching the tubing to reduce its thickness to a desired level; and heating the stretched tubing to thereby adhere the tubing wire.

In accordance with a still further aspect of the invention, ablation guide wire tip structures are provided to more efficiently ablate occlusive tissue using a decreased amount of RF power. Towards this end, an ablative guide wire assembly includes an elongate conductive guide wire having an ablation tip formed on its distal end, the ablation tip having a generally non-traumatic structure with a discontinuous feature.

By way of non-limiting example, the non-traumatic tip structure may be spherically shaped, wherein the discontinuous feature comprises one or more protrusion(s) or edge(s) formed on the structure to thereby form high current densities at the discontinuous points. The high current density provides a corresponding high power density, resulting in more efficient tissue ablation.

In accordance with a still further aspect of the invention, a distal portion of the guide wire is shapeable such that the distal portion of the guide wire can better track through, for example, a curved blood vessel lumen.

In accordance with yet a further aspect of the invention, electrical energy pulses are supplied from an RF generator to a monopolar guide wire electrode tip in a continuous wave form, each pulse having an initially high spike, but with the RMS voltage maintained at a relatively low level. In particular, the guide wire ablation system output voltage and impedance are selected in conjunction with the electrode tip geometry (i.e., depending on the particular current density achieved at the electrode tip) to provide for optimal spark erosion when the electrode tip is in contact with high impedance occlusive tissue, while reducing the overall power output when in contact with blood or healthy vessel wall tissue Other and further objects, features, aspects, and advantages of the present invention will become better understood with the following detailed description of the accompanying drawings.

BRIEF DESCRIPTION OF THE DRAWINGS

The drawings illustrate both the design and utility of preferred embodiments of the present invention, in which:

FIG. 12 is a circuit schematic of the generator of FIG. 1;

FIG. 12A is a voltage wave signal output by the generator system of FIG. 12;

FIG. 33 is a cut away, partial side view of still another centering catheter employed in the vessel recanalization system of FIG. 1, wherein the centering catheter particularly employs a plurality of resilient centering rings as a centering mechanism;

FIG. 33A is a cross-sectional view of the centering catheter of FIG. 33 taken along the line 33A—33A;

DETAILED DESCRIPTION OF THE PREFERRED EMBODIMENTS

Figure 1:
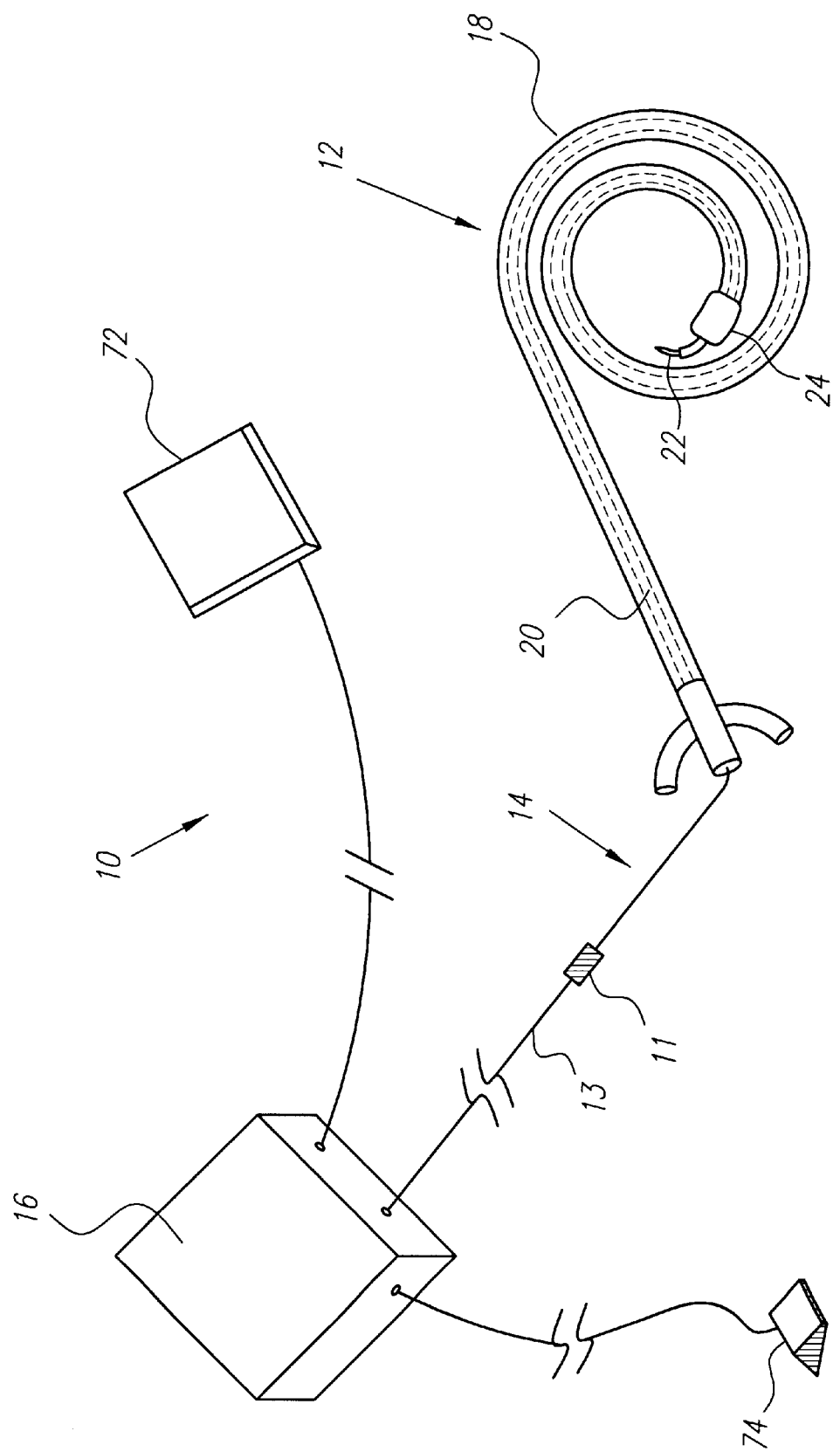
FIG. 1 is a perspective view of a vessel recanalization system.

FIG. 1 depicts a preferred embodiment of a vessel recanalization system 10 constructed in accordance with the present invention. The system 10 generally includes a centering catheter 12, an ablative guide wire 14, and a radio frequency (RF) generator 16, which are arranged to facilitate the therapy of a totally occluded blood vessel 250 (shown with an occlusion 252 in FIGS. 13–16) within a patient.

The centering catheter 12 includes an elongated catheter body 18 with a guide wire lumen 20 through which the ablative guide wire 14 is slidingly disposed. The ablative guide wire 14 includes a distal ablation tip 22, which may be extended from the distal end of the catheter body 18. The centering catheter 12 further includes a centering mechanism 24 mounted to the catheter body 18 adjacent the guide wire lumen 20 for centering the distal ablation tip 22 within the blood vessel 250.

The proximal end of the ablative guide wire 14 is coupled via a connector 11 to an RF supply cable 13 from the generator 16. The generator 16 provides RF energy to the guide wire ablation tip 22 for spark-erosion assisted recanalization of the occlusion 252. The energy is returned through a patient return electrode 72, which is also electrically coupled to the generator 16. Preferably, the patient return electrode 72 takes the form of a pad with a substantially large area, so that the delivery of RF energy to the target tissue is maximized. In accordance with known RF generator systems, a footswitch control 74 is used to control output of the generator 16 i.e., wherein depression of the footswitch 74 provides a controlled delivery of RF energy from the generator 16 to the guide wire ablation tip 22.

While the ablative guide wire 14 is configured as a mono-polar electrode, those with skill in the art will recognize that a bi-polar configuration may also be employed. In a bi-polar configuration, the return electrode would be positioned in close proximity to the ablation tip electrode 22. For example, a tubular return electrode may be disposed around the tip of catheter 18 proximate its distal end. A mono-polar arrangement is preferred, because it allows for a lower profile, ——i.e., no return wire is needed in the catheter 18. It is conceivable, however, to design a bi-polar device wherein the return conductor can be contained within an acceptable profile.

Figure 2:
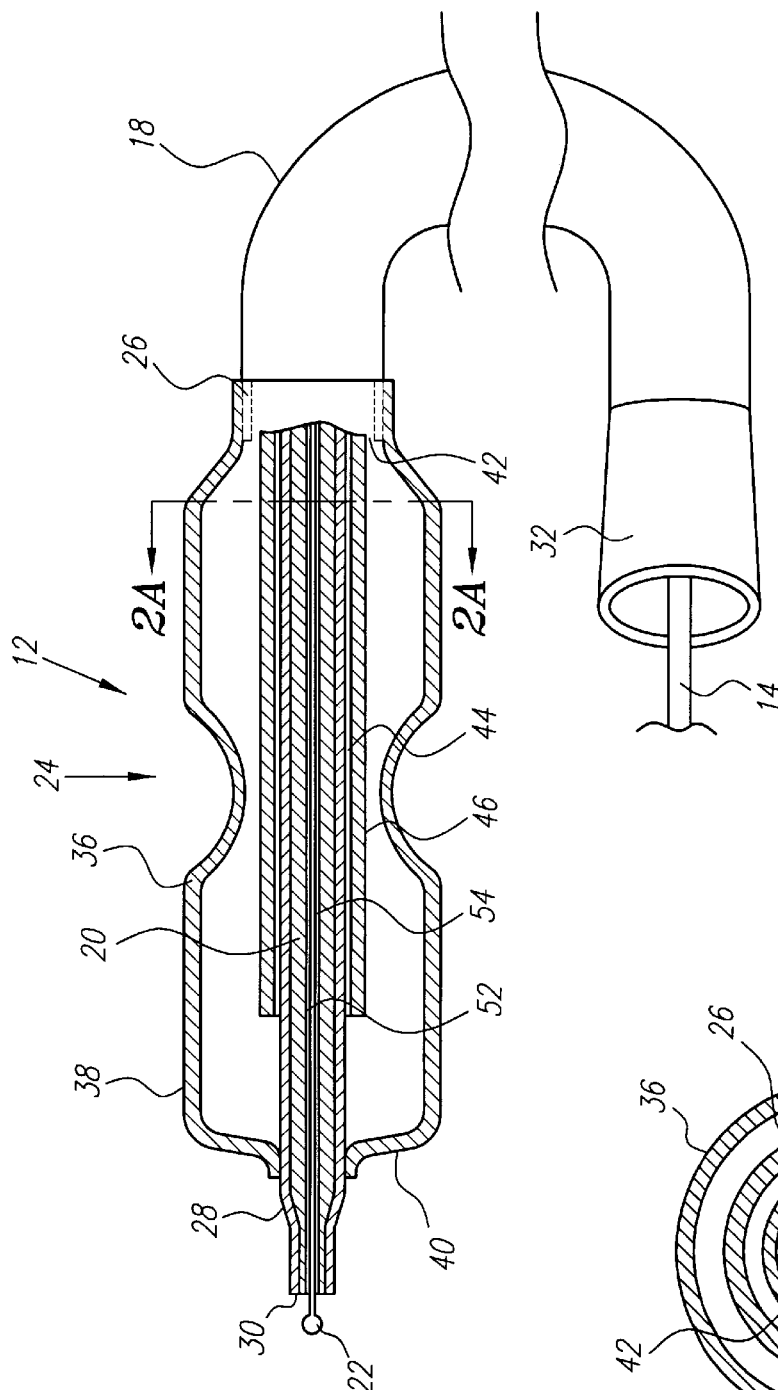
FIG. 2 is a cut away, partial side view of a first preferred centering catheter used in the vessel recanalization system of FIG. 1.
Figure 2A:
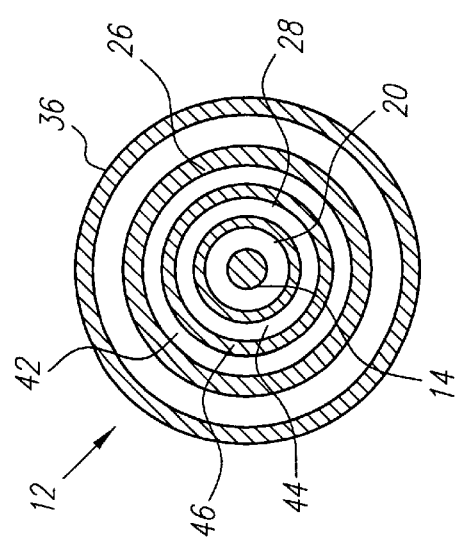
FIG. 2A is a cross-sectional view of the centering catheter of FIG. 2 taken along the line 2A—2A.

Referring to FIG. 2, the centering catheter 12 is particularly described. The catheter body 18 of the centering catheter 12 includes an elongated flexible outer jacket 26 and an elongated flexible inner shaft 28 extending therethrough. The outer jacket 26 and inner shaft 28 are preferably composed of a suitable soft and flexible material to minimize the bias around the curvilinear regions of the patient's vasculature.

Preferably, the inner shaft 28 is composed of a radio-opaque material, which both facilitates the location of the distal ablation tip 22 within the blood vessel 250 and enhances the collapsing strength of the inner shaft 28. Such radio-opaque material can be created by compounding heavy metal particles, such as, e.g., 80% (by weight) tungsten added to Marlex 4903 (high density polyethylene), into a thermal plastic. The guide wire lumen 20 is formed in the inner shaft 28 and extends therethrough distally terminating at a guide wire exit port 30. Centering catheter 12 includes a female Luer fitting 32 formed at the proximal end of the catheter body 18, which mates with an adapter 34 (shown in FIG. 11).

As will be described in further detail below, the centering mechanism 24 of the centering catheter 12, when activated, facilitates the centering of the distal ablation tip 22 within the blood vessel 250, and when deactivated, allows the catheter body 18 to be longitudinally displaced within the blood vessel 250. The centering mechanism 24, in a preferred embodiment, particularly includes a single inflatable/deflatable balloon 36, which is preferably elongated for purposes of stability.

The balloon 36 is composed of a suitable material, such as, e.g., polyamides, polyimides, nylons, and polyether block amide, which is commercially available from, e.g., Atomchel Polymers of Bindsboro, Pa. under the trade name PEBAX, and is affixed to the distal end of the catheter body 18. In particular, the proximal end of the balloon 36 is secured to the distal end of the outer jacket 26, and the distal end of the inflatable balloon 36 is secured to the distal end of the inner shaft 28. Preferably, the balloon 36 is compliant to facilitate the centering of the distal ablation tip 22 within variably sized blood vessels.

A distal side 38 of the balloon 36 includes a shoulder 40 with a substantially vertical profile, i.e., a profile substantially perpendicular to the longitudinal axis of the centering catheter 12. The vertical profile of the shoulder 40 allows the distal ablation tip 22 to be located closer to the portion of the balloon 36 contacting the wall of the blood vessel 250 ensuring that the distal ablation tip 22 is centered as it exits the guide wire exit port 30.

The centering catheter 12 further comprises an inflation lumen 42 formed between outer jacket 26 and sheath 46 of the catheter body 18, i.e., the inflation lumen 42 is annular. The inflation lumen 42 terminates proximally at the adapter 34 and distally within the balloon 36. Conveyance of a suitable inflation medium, such as, e.g., saline solution, into the inflation lumen 42 expands the balloon 36, thereby activating the centering mechanism 24. Contrariwise, conveyance of the inflation medium from the inflation lumen 42 collapses the balloon 36, thereby deactivating the centering mechanism 24.

The centering catheter 12 further comprises an airless preparation lumen 44 disposed between inner shaft 28 and sheath 46 and terminating distally within the balloon 36. As will be described in further detail below, the airless preparation lumen 44 provides a convenient means of removing air from the balloon 36 and positively preparing the balloon 36 for subsequent inflation. It should be noted that the airless preparation lumen 44 can be employed in conjunction with the inflation lumen 42 to prepare other types of balloon catheters, such as, e.g., PTCA catheters, and is not to be limited to employment within a centering catheter.

That is, inflation medium can be conveyed through the airless preparation lumen 44, into the balloon 36, and back out the inflation lumen 42, eliminating the need to bleed inflation medium at the tip of the centering catheter 12 or evacuating air from the balloon 36 prior to inflation thereof. Preferably, the inflation lumen 42 and the airless preparation lumen 44 terminate within the balloon 36 opposite each other ensuring that substantially all of the air is removed from the balloon 36 during the preparation thereof.

Disposition of the airless preparation lumen 44 within the inflation lumen 42 allows the catheter body 18 to be manufactured with a smaller profile, decreasing the amount of stress of the patient's vasculature as it advances therethrough. Additionally, the independence of the outer jacket 26 and sheath 46 allows the catheter body 18 to be more easily manufactured as compared to standard dual-lumen catheters. This concentric design also provides for a lower profile of catheter body 18.

Figure 3:
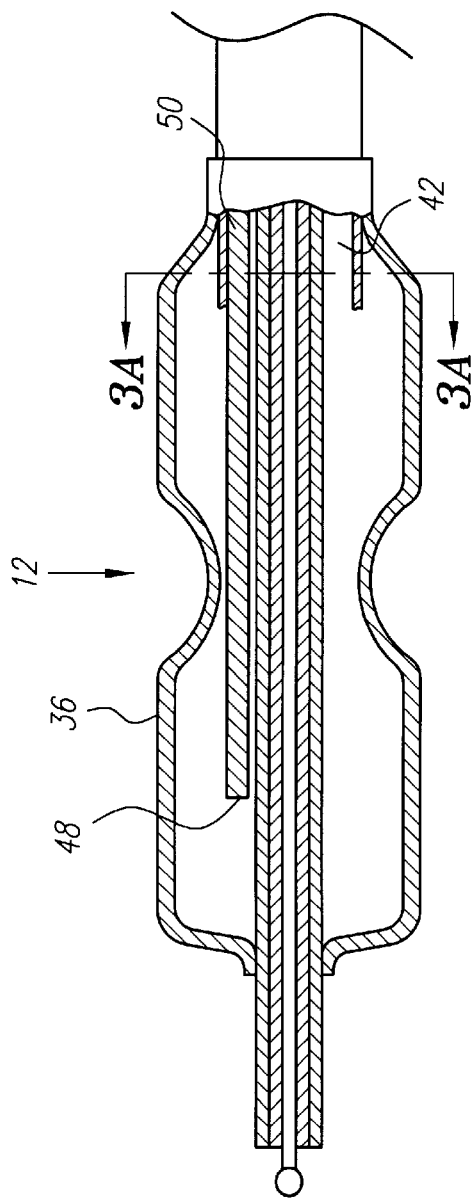
FIG. 3 is a partial side view of an another preferred centering catheter of FIG. 2.
Figure 3A:
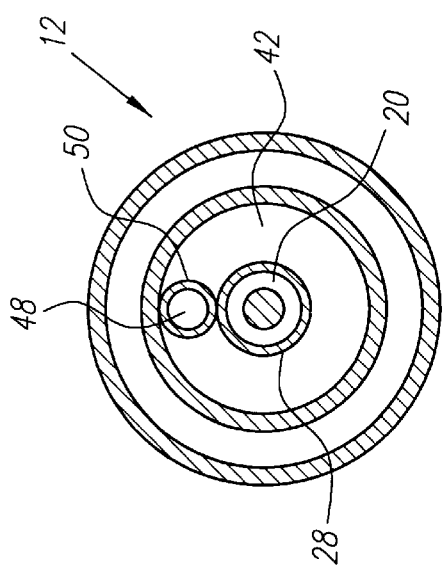
FIG. 3A is a cross-sectional view of the centering catheter of FIG. 3 taken along the line 3A—3A.

As seen in FIG. 2, the airless preparation lumen 44 is formed between sheath 46 and the inner shaft 28, i.e., the airless preparation lumen 44 is annular. Alternatively, as shown in FIG. 3, the centering catheter 12 comprises an airless preparation lumen 48 formed solely within a flexible elongated tube 50 independent of the inner shaft 28, i.e., the airless preparation lumen 48 is circular.

The ablative guide wire 14 extends through the guide wire lumen 20 of the inner shaft 28 of the catheter body 18, with the distal ablation tip 22 of the guide wire 14 extending out the guide wire exit port 30 of the guide wire lumen 30 for placement in contact with body tissue. The diameter of the guide wire 14 is sized, such that it is compatible for use with Percutaneous Transluminal Coronary Angioplasty (PTCA) and/or Percutaneous Transluminal Angioplasty (PTA) catheters, as well as other diagnostic and therapeutic devices.

In this connection, the guide wire 14 is relatively small, having a diameter of from about 0.004 to 0.030 inches. Exemplary diameters are 0.014 inches to provide compatibility with standard PTCA catheters, and 0.009 inches to provide compatibility with atherectomy catheters, such as, e.g., the Rotablator® system. Preferably, the guide wire 14 has an exemplary length consistent with that of a PTCA guide wire, i.e., 300 cm.

Figure 4:
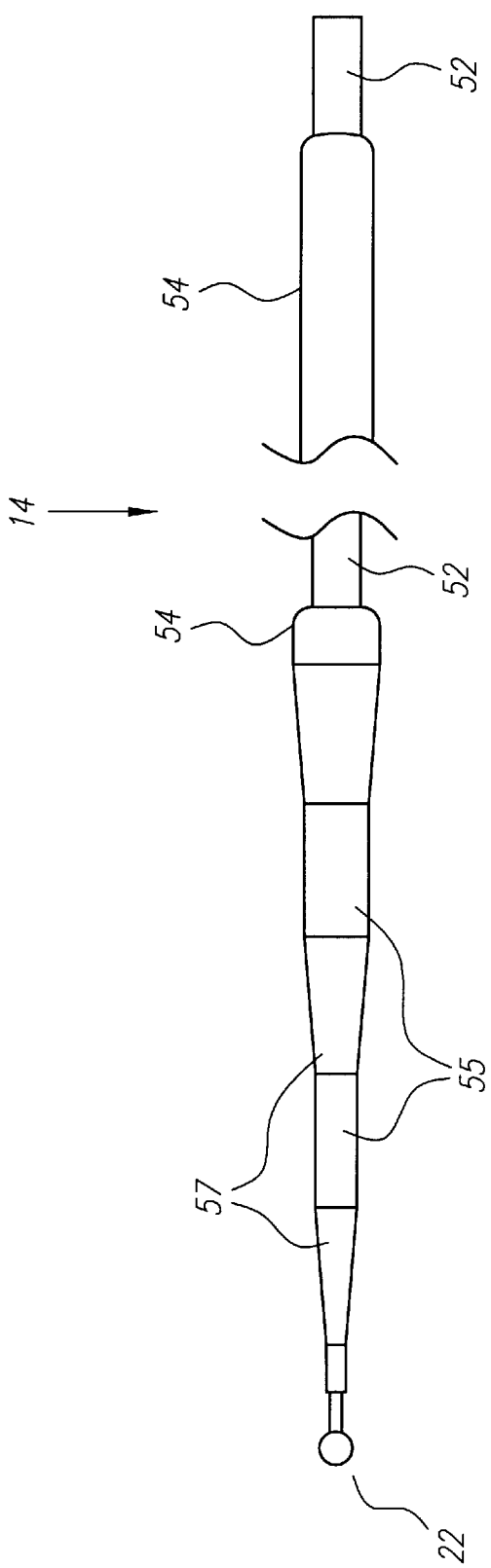
FIG. 4 is a side view of an ablative guide wire employed in the vessel canalization system of FIG. 1.

Referring further to FIG. 4, the guide wire 14 comprises an elongate shaft 52 composed of a suitable material, such as, e.g., 3XX series stainless steel, cobalt alloys, nickel titanium alloys, or combinations of tungsten/gold with stainless steel or cobalt alloys, to provide high strength and corrosion resistance. The guide wire 14 further includes a layer of electrical insulation 54 formed at the proximal and distal ends of the shaft 52.

The distal ablation tip 22 is bare of the insulation 54, allowing conveyance of RF energy between the distal ablation tip 22 and the tissue. The portion of the shaft 52 between the proximal and distal ends thereof is bare of the insulation 54, since the inner shaft 28 provides electrical insulation to the guide wire 14 when the guide wire 14 is disposed within the guide wire lumen 20.

A proximal tip of the shaft 52, approximately one-half inch, is bare of the insulation 54, allowing electrical connection to the connector 11 (FIG. 1). The insulation 54, along with the inner shaft 28, facilitates the effective delivery of RF power to the distal ablation tip 22 by restricting the dissipation of the RF energy to the distal ablation tip 22.

Preferably, the insulation 54 is at least 0.001 inches thick to sustain the level of RF energy that will be conducted through the shaft 52 (generally about 20–30 watts). The insulation 54 is composed of suitable bio-compatible material, such as, e.g., polytetrafluoroethylene (PTFE) (available as TEFLON® from E.I. Dupont), polyimide and polyester. PTFE and polyester can be formed onto the shaft 52 as heat shrink tubes, while polyimide and TEFLON® can be formed onto the shaft 52 as a dip coating or spray coating. Preferably, however, heat shrink tubing is used as it provides the best control of thickness uniformity and freedom from pin hole like defects.

Figure 5:
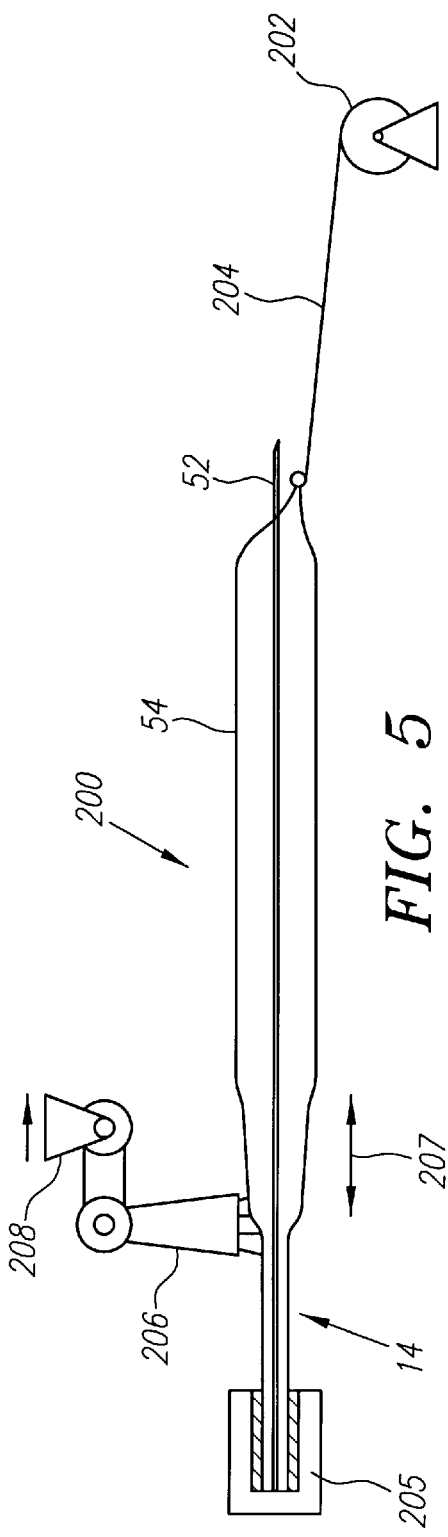
FIG. 5 is a plan view of an insulation application machine used to manufacture the ablative guide wire of FIG. 4.

Referring to FIG. 5, an insulation application machine 200 is employed to apply insulation 54 to the shaft 52 using heat shrink tubing. The insulation application machine 200 comprises a motorized pull system 202 configured to stretch the heat shrink tubing to a desired thickness. The heat shrink tubing is connected to the motorized pull system 202 via a pull string 204. The insulation application further includes a hot air gun 206 mounted on a computer controlled traveling stage 208, and is thus configured to longitudinally translate the length of the heat shrink tubing (shown by arrow 207) while heating the same to a desired temperature at the same time. The motorized pull system 202 incudes a clamp 205, which anchors one end of the heat shrink tubing to the shaft 52 while the heat shrink tubing is being stretched.

In operation, the proximal end of the heat shrink tubing is anchored to one end of the shaft 52, using the clamp 205. The heat shrink tubing is then disposed over the shaft 52, the distal end of which is connected to the motorized pull system 202 via the pull string 204. The motorized pull system 202 is then operated, stretching the heat shrink tubing to a desired thickness. In this manner, the resulting insulation 54 is thinned, ensuring compatibility between the guide wire 14 and any associated therapeutic catheter. Simultaneous with or subsequent to the stretching, the hot air gun 206 and travelling stage 208 is operated to heat the length of the stretched heat shrink tubing, preferably between 650° F. and 800° F., thereby adhering the heat shrink tubing to the shaft 52 to form the ablative guide wire 14. Preferably, because the catheter body 18 provides insulation to the guide wire 14, only the distal and proximal ends of the guide wire 14 are insulated with the heat shrink tubing, maximizing the thickness of the shaft 52 and improving the electrical property of the guide wire 14. Exemplary insulated lengths of the distal and proximal ends of the guide wire 14 are respectively, 15 and 100 cms.

Referring back to FIG. 4, the distal end of the guide wire 14, preferably the distal six to eighteen inches, is tapered to provide steerability and flexibility to the guide wire 14. In particular, the tapered portion of the guide wire 14 includes a combination of alternating cylindrical sections 55 and tapered sections 57. Preferably, the distal end of the guide wire 14 exhibits enough rigidity, such that it can be configured to assume a curvilinear geometry (i.e., shapeable). In this manner, the distal ablation tip 22 can be safely and efficiently translated through a curvilinear region of the vessel 250 during ablation.

Preferably, the distal end of the guide wire 14 includes a latinum allow spring to provide the guide wire 14 with radio paqueness. Alternatively, the distal end of the guide wire 14 can include a resilient polymer jacket impregnated with radio-opaque material. More alternatively, radio opaqueness can be provided to the guide wire 14 by applying a radio opaque coating, such as, e.g., gold, to the distal end thereof.

Referring to FIGS. 6–10, the distal ablation tip 22 of the guide wire 14 includes a non-traumatic structure 56, such as, e.g., a spherically shaped structure (i.e., a ball or half-ball), to minimize tissue trauma, while localizing RF energy conveyed through the guide wire 14 to allow initiation and maintenance of tissue ablation at low RF power levels.

The distal ablation tip 22 includes at least one discontinuous feature 58 associated with the structure 56, such as, e.g., an edge or point, to further facilitate the sparking between the distal ablation tip 22 and the tissue as will be described in further detail below. Towards this end, various ablation tips 22 will be described with reference to FIGS. 6–10.

Figure 6:
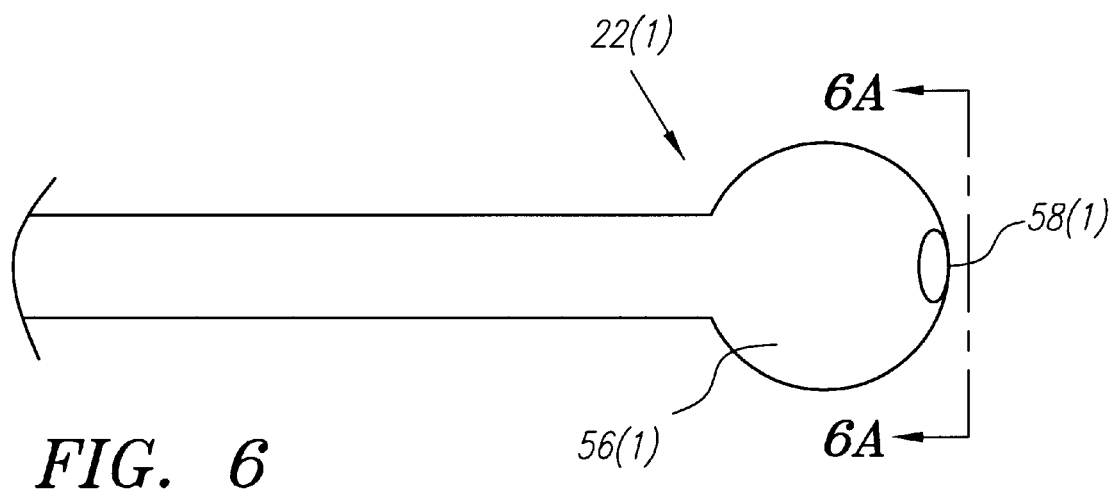
FIG. 6 is a partial side view of a distal ablation tip employed by the ablative guide wire of in FIG. 4.
Figure 6A:
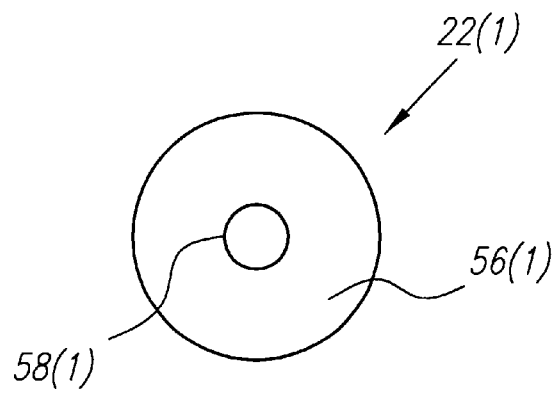
FIG. 6A is a front view of the distal ablation tip of FIG. 6 taken along the line 6A—6A.

FIG. 6 depicts an ablation tip 22(1), which includes a structure 56(1) in the form of a ball. The distal ablation tip 22(1) further includes a discontinuous feature 58(1) in the form of a shallow cavity with a circumferential edge disposed on the non-traumatic structure 56(1). In this manner, the distribution of RF energy along the surface of the structure 56(1) is localized along the edge of the discontinuous feature 58(1).

Figure 7:
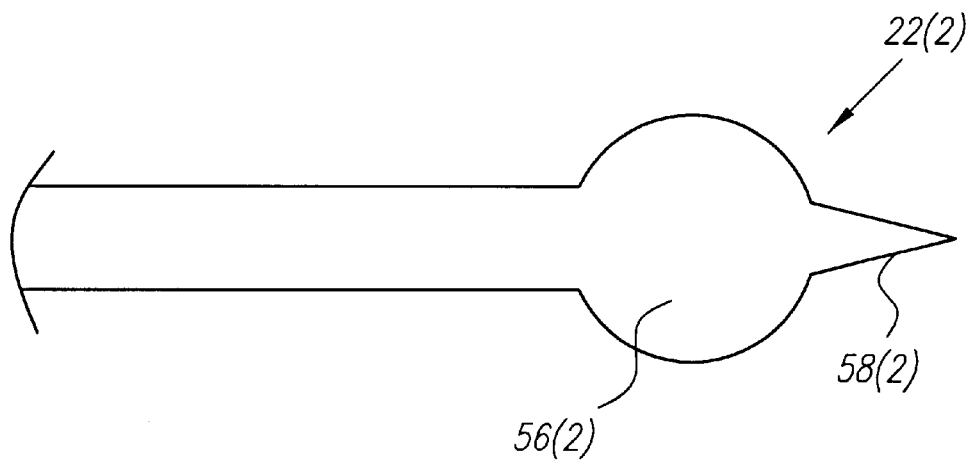
FIG. 7 is a partial side view of another distal ablation tip employed by the ablative guide wire of FIG. 4.

FIG. 7 depicts an ablation tip 22(2), which includes a structure 56(2) in the form of a ball. The distal ablation tip 22(2) further includes a discontinuous feature 58(2) in the form of a point disposed on the non-traumatic structure 56(2). In this manner, the distribution of RF energy along the surface of the structure 56(2) is localized at the point of the discontinuous feature 58(2).

Figure 8:
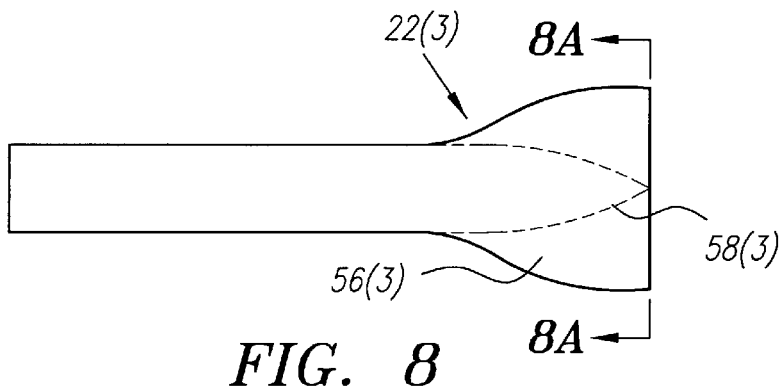
FIG. 8 is a partial side view of still another distal ablation tip employed by the ablative guide wire shown in FIG. 2.
Figure 8A:
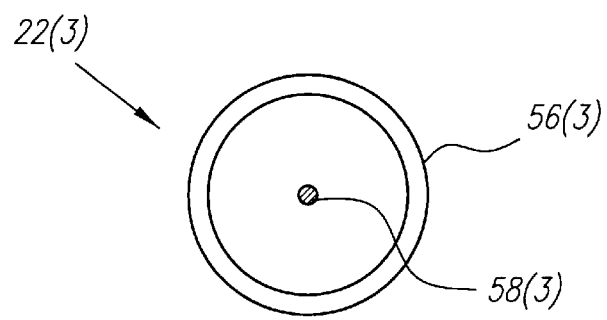
FIG. 8A is a front view of the distal ablation tip of FIG. 8 taken along the line 8A—8A.

FIG. 8 depicts an ablation tip 22(3), which includes a hollow bell-shaped structure 56(3). The distal ablation tip 22(3) further includes a discontinuous feature in the form of a point disposed within the structure 56(3). The structure 56(3) is electrically insulated. In this manner, the distribution of RF energy is localized at the point of the discontinuous feature 58(3).

Figure 9:
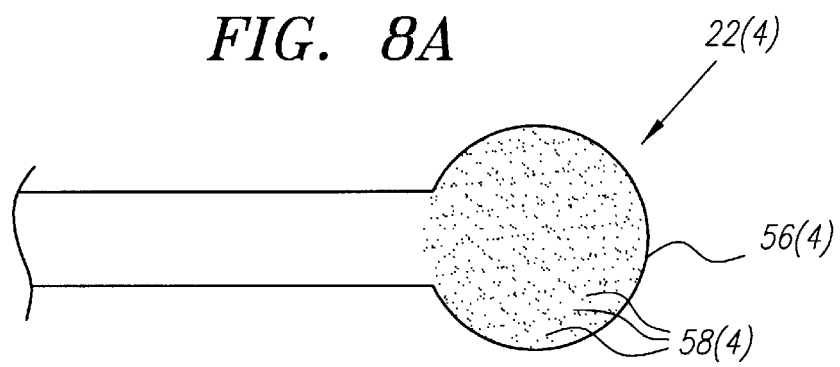
FIG. 9 is a partial side view of still another distal ablation tip employed by the ablative guide wire of FIG. 4.

FIG. 9 depicts an ablation tip 22(4), which includes a structure 56(4) in the form of a ball. The distal ablation tip 22(4) further includes a plurality of discontinuous features 58(4) in the form of microscopic roughened points or edges, which is applied to the outer surface of the structure 56(4) by suitable means, such as, e.g., etching, film deposition, or grit blasting. In this manner, the distribution of RF energy along the structure 56(4) is localized at the roughed points or edges of the discontinuous features 58(4).

Figure 10:
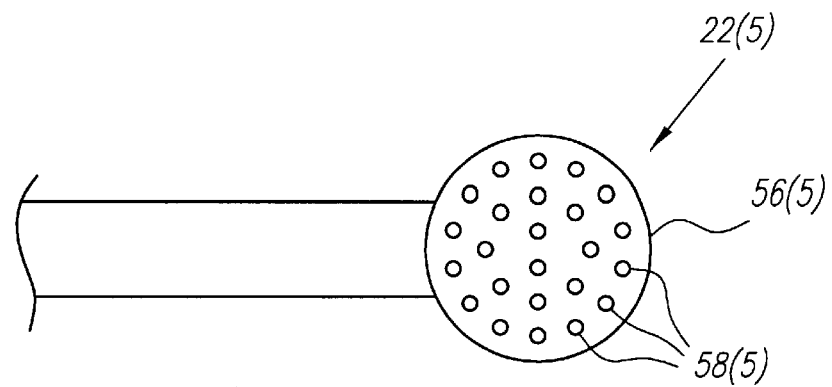
FIG. 10 is a partial side view of still another distal ablation tip employed by the ablative guide wire of FIG. 4.

FIG. 10 depicts an ablation tip 22(5), which includes a structure 56(5) in the form of a ball. The distal ablation tip 22(5) further includes a plurality of discontinuous features 58(5) in the form of microscopic non-conducting particles disposed on the outer surface of the structure 56(5). The dispersion of the non-conducting particles serves to reduce the effective cross-sectional area of the structure 56(5). In this manner, the distribution of RF energy along the structure 56(5) is localized between the non-conducting particles.

Figure 11:
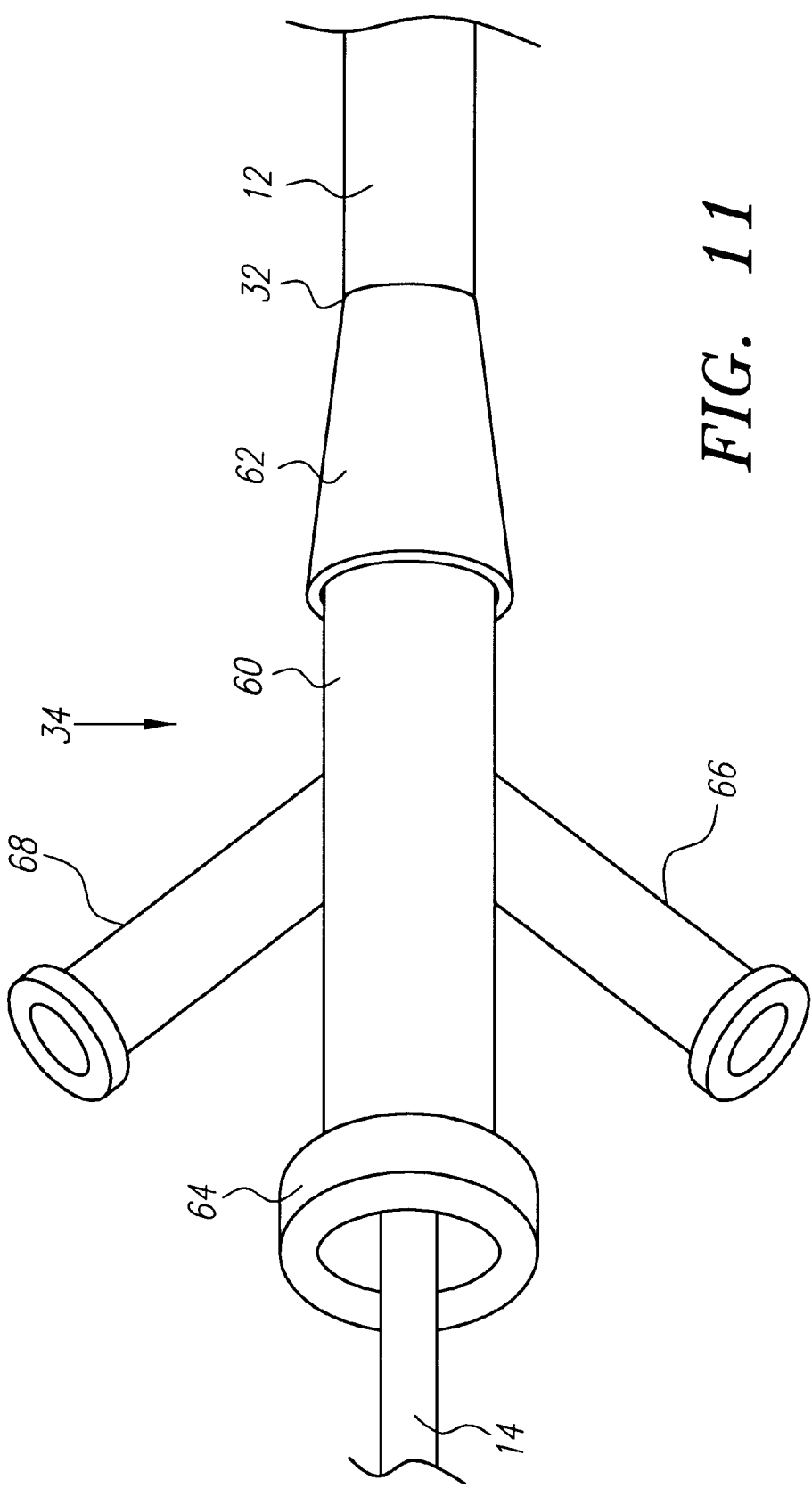
FIG. 11 is a perspective view of a proximal adapter, particularly shown mated to the proximal end of the centering catheter of FIG. 2.

FIG. 11 particularly shows the adapter 34, which mates with the female Luer fitting 32 of the catheter 12. The adapter 34 includes a body 60 with a male Luer fitting 62 on a first end and a gland nut 64 on a second end. The guide wire 14 passes through both male Luer fitting 62 and the gland nut 64. Feeding is continued until the female Luer fitting 32 on the catheter 12 is engaged with the male Luer fitting 62 of the adapter 34. The gland nut 64 on the adapter 34 is tightened to secure the guide wire 14 in place relative to the catheter 12 and to prevent loss of fluid at the point where the guide wire 14 exits the adapter 34. Relative positioning of the distal ablation tip 22 of the guide wire 14 to the guide wire exit port 30 of the catheter body 18 is accomplished by loosening the gland nut 64.

The adapter 34 further includes an inflation port 66 and a preparation port 68, which are respectively in fluid communication with the inflation lumen 42 and the airless preparation lumen 44. The inflation port 66 provides a means for conveying an inflation medium into the inflation lumen 38 during expansion of the balloon 36, and the preparation port 68 provides a means for removing air from the balloon 36.

Referring to FIG. 12, the RF generator 16 includes a source of energy 70, which is approximately twenty to thirty watts in a preferred embodiment. The source of energy 70 is selectively coupled via the footswitch 74 to a primary winding 171 of an isolating transformer 172. In accordance with known power supply techniques, transfer of energy from the primary winding 171 to the transformer core 175 is driven by an NMOS transistor switch 174. The NMOS switch 174 is cyclically driven ON and OFF by an oscillator circuit 176, preferably at a frequency of 500 KHz or higher to avoid interference with the normal electrical stimulation of the heart.

The respective primary and secondary transformer windings 171 and 173 are configured in a flyback mode. When the NMOS transistor 174 is ON, current passes through the primary winding 171 and energy is stored in the transformer core 175. When the NMOS transistor is turned OFF, energy stored in the core 175 is released in the form oof current through the secondary winding 173.

In particular, when NMOS transistor 174 turns OFF, the voltage at the NMOS drain increases significantly. This is because the voltage across the transformer 172 is proportionate to the time-derivative of the current passing through the primary winding 173. Since the current is forced to cease when the NMOS transistor 174 turns OFF, (but does not in fact immediately cease), the corresponding time-derivative has a very high value at this point. This, in turn, causes the voltage across the transformer core 175 to increase substantially, resulting in a voltage "spike" through the secondary each time the NMOS transistor 174 is turned OFF at the beginning of each new energy transfer cycle, or pulse.

The output voltage signal 190 through the secondary winding 173 of the transformer 172 is shown in FIG. 12A, as a series of discrete pulses, each pulse having a respective voltage spike 192 at its leading edge. In a preferred embodiment, the output signal pulses have voltage spikes 192 of approximately five to ten times higher in amplitude than the RMS output voltage of the signal 190. The output voltage signal 190 is preferably supplied for a discrete duration, e.g., 1–2 seconds, each time the foot switch 74 is activated.

As would be appreciated by those skilled in the art, any number of power supply topologies (e.g., a forward topology) may be used to achieve a voltage output signal having the general form of signal 190 without departing from the invention. What is important is that the discrete pulses have the momentary peak amplitude to provide a high sparking potential at the guide wire ablation tip 22, without unduly increasing the overall RMS voltage of the signal. Alternately, the voltage spikes 192 could be generated only when needed to initiate the spark erosion process, with the output signal otherwise being an attenuated waveform, such as squared cosine.

Referring still to FIG. 12, a pair of capacitors 178 and 180 are provided in series with the circuit formed through the patient by the respective ablation and patient return electrodes 22 and 72 on the output side of the transformer 172. In particular, the capacitors 178 and 180 are sized to set the generator system output impedance "seen" at the guide wire ablation tip 22. For patient safety purposes, the capacitors 178 and 180 also serve to limit the maximum voltage delivered to the patient tissue, according to the relationship:

$|V|_{tissue} = V_{source} (Z_{tissue}/(Z_{tissue}+Z_c))$, where $Z_{tissue}$ is the load impedance of the tissue or blood contacting the ablation electrode and $Z_c$ is total impedance value of the series capacitors 178 and 180. Although two capacitors are used for greater control (i.e., more predictable tolerance) in the illustrated preferred embodiment, a single capacitor (i.e., capacitor 178) would work.

In a preferred embodiment, capacitors 178 and 180 are sized to set the system output impedance to a level greater than the load impedance of blood and healthy vessel wall tissue in order to reduce the power output when the ablation electrode 22 is not in contact with the (high impedance) occlusive matter. In particular, it is desirable to achieve a high current density at the distal tip of the ablation electrode 22 for initiating the spark erosion process, without requiring maximum output power from the generator 16.

Figure 12B:
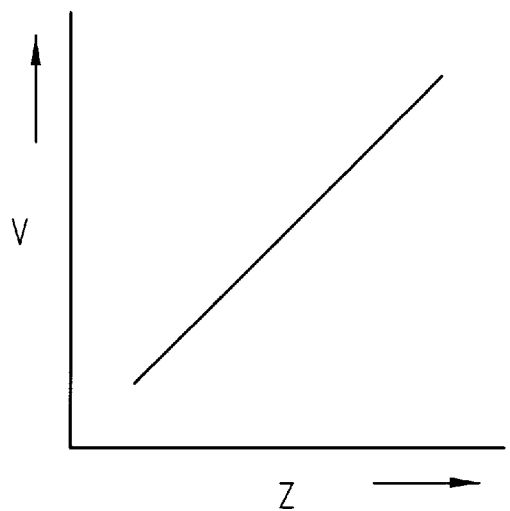
FIGS. 12B–D illustrate the relationships between the system output voltage, current and power, respectively, versus patient tissue load impedance "seen" at the guide wire ablation tip.
Figure 12C:
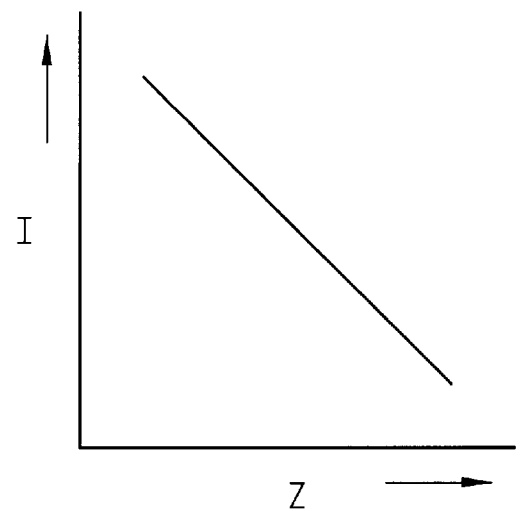
Figure 12D:
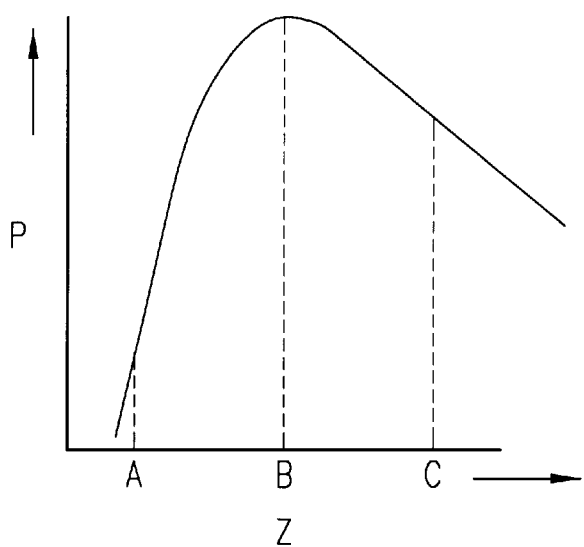

FIGS. 12B–D illustrate the respective relationships between the output current, voltage and power, respectively, of the generator versus the load impedance "seen" at the guide wire ablation electrode 22. As seen in FIG. 12B, the output voltage is directly proportional to the load impedance, i.e., the higher the load impedance, the greater the voltage potential. Conversely, as seen in FIG. 12C, the output current is inversely proportional to the load impedance, i.e., as the load impedance increases, the output current decreases. On the other hand, the output power of the generator 16 is dependent upon the relative impedance match been the electrode tip 22 and the load impedance.

FIG. 12D shows the relationship between output power of the generator 16 versus the load impedance seen at the electrode tip 22 for a system impedance (i.e., as set by capacitors 178 and 180) of approximately 600 ohms. At point A, the generator is activated with the electrode tip in contact with blood (150–200 ohm/cm). Because the impedance is low, the voltage potential is also low enough that the spark erosion process is not initiated, although a relatively high current due to the impedance mismatch is contributing to a small amount of ohmic heating at the electrode tip. By choosing the appropriate electrode geometry, however, tissue or blood necrosis from the ohmic heating from the current can be minimized. In particular, the benefits of reducing power output when the electrode tip 22 is in contact with blood or healthy vessel wall tissue in terms of reduced tissue damage and/or potential for unwanted ablation or charring are believe to far exceed the possible damage caused by ohmic heating at low load impedance levels.

At point B, the output power is maximized with the electrode in "close contact" with occlusive tissue resulting in a load impedance of approximately 600 ohm/cm, i.e., substantially matching the generator system impedance. In a preferred embodiment, the generator voltage, impedance and electrode geometry (i.e., current density at the tip 22) are selected such that the spark erosion process will be initiated at a load impedance greater than blood and/or healthy vessel tissue —i.e., near point B in FIG. 12D.

Once the spark is initiated, it is possible that the load impedance will increase substantially ——e.g., to a range of 1800–2000 ohm/cm, ——or decrease substantially, ——e.g., least than 50 ohm/cm, ——depending upon the ionization charge density of the plasma state and the relative position of the electrode tip 22. If the impedance increases, the sparking voltage potential will be maintained, even though the power output will decrease (i.e., past point C in FIG. 12D). If the impedance drops, the voltage potential and power output will also drop (e.g., to the left of point A in FIG. 12D), although the plasma state will be maintained at a much lower voltage potential than is required for its initiation. In other words, like florescent lighting, a relatively high voltage potential at the electrode tip 22 is needed to initiate a spark and convert the occlusive matter into a plasma state, it may be maintained in this state with a relatively low voltage potential, as the guide wire tip is moved through the occlusive matter by lateral force applied by the surgeon (explained in greater detail below).

Figure 12E:
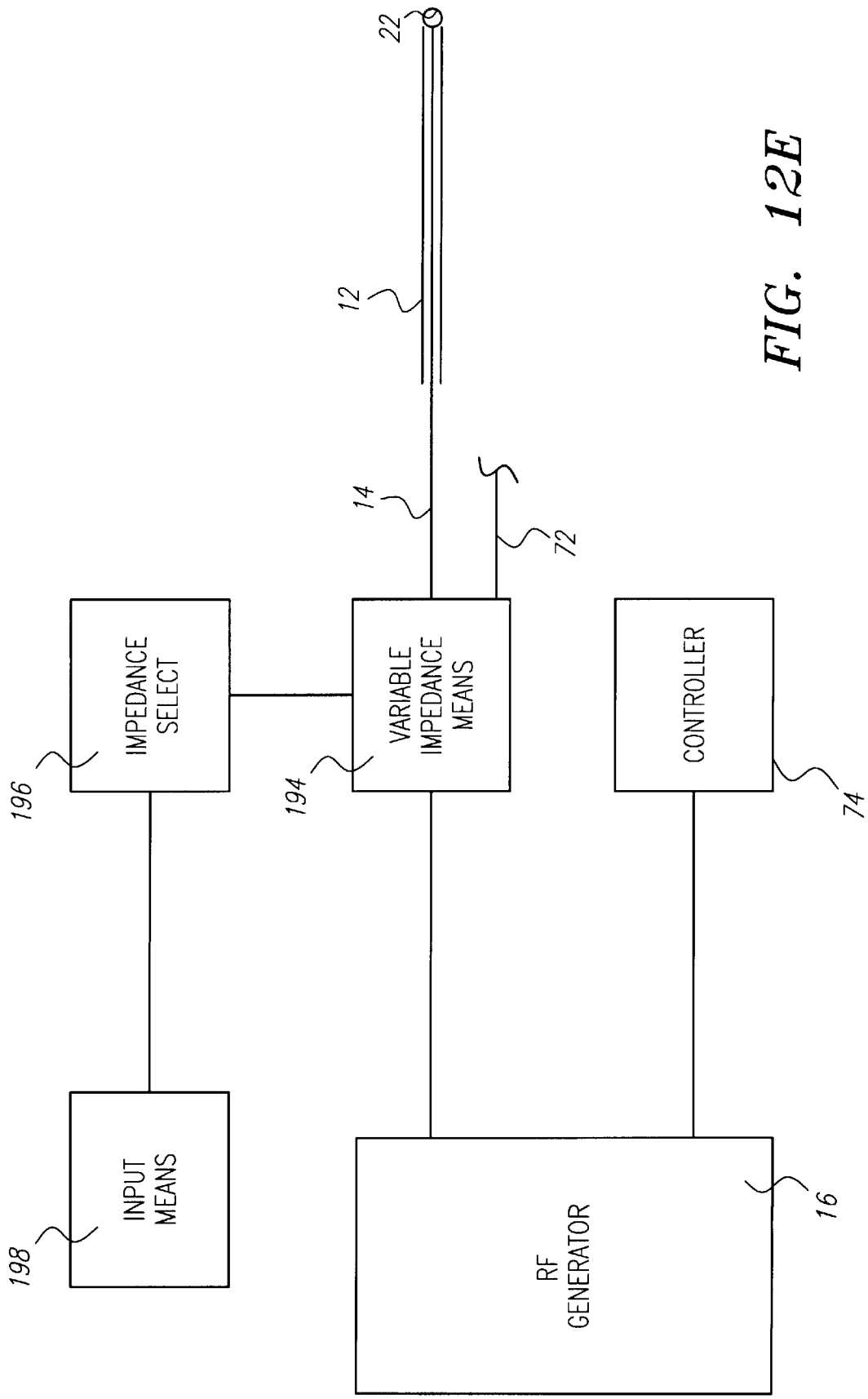
FIG. 12E is a simplified functional block diagram of impedance control elements in an alternate recanalization system.

Referring to FIG. 12E, an alternate preferred embodiment of the recanalization system 100 includes a variable impedance means 194 coupled at the output of the RF generator 16, i.e., in addition to, or in lieu of, capacitors 178 and 180. The variable impedance means 194 is coupled to an impedance selection means 196, which in turn is coupled to an input means 198. The input means 224 provides an attending surgeon or other user of the recanalization system to enter information pertaining to the specific procedure being performed, such as, e.g., the type or model number of centering catheter 12 and/or ablation guide wire 14, the geometric design or surface area of the ablation electrode 22, the weight of the patient, the desired voltage, etc.

The variable impedance means 194 may include active or passive components such as capacitors, inductors, resistors, and transistors or any combination thereof. In a presently preferred embodiment, the variable impedance means 194 is comprised of a network of capacitors and solid state switching devices. In this presently preferred embodiment, the impedance of variable impedance means may be varied by switching capacitors into, or out of, the network.

The actual impedance value of variable impedance means 194 is selected by the impedance selection means 196. In the just-described preferred embodiment, the impedance selection means 196 controls the state of the respective solid state switches within the variable impedance means 194. In particular, information entered into the recanalization via the input means 198 may be utilized to select an appropriate value for variable impedance means 194. In a presently preferred embodiment, the impedance value selected by impedance selection means 196 is based at least in part on the geometry of the particular ablation electrode 22 being used for the procedure.

The impedance selection means 196 may also include stored information useful for selecting an appropriate impedance value, such as impedance values appropriate for each model of guide wire and/or voltage level. Other factors may be used in determining appropriate impedance values without deviating from the spirit or scope of the present invention. In any case, the impedance value of variable impedance means 196 is preferably selected so that maximum voltage power transfer occurs when the ablation electrode 22 is in contact with occlusive lesion tissue.

Operation of the vessel recanalization system 10 to centrally recanalize a total occlusion 252 disposed in the blood vessel 250, and in particular, a rectilinear region 254 of the blood vessel 250, is now described with reference to FIGS. 13–18.

Figure 13:
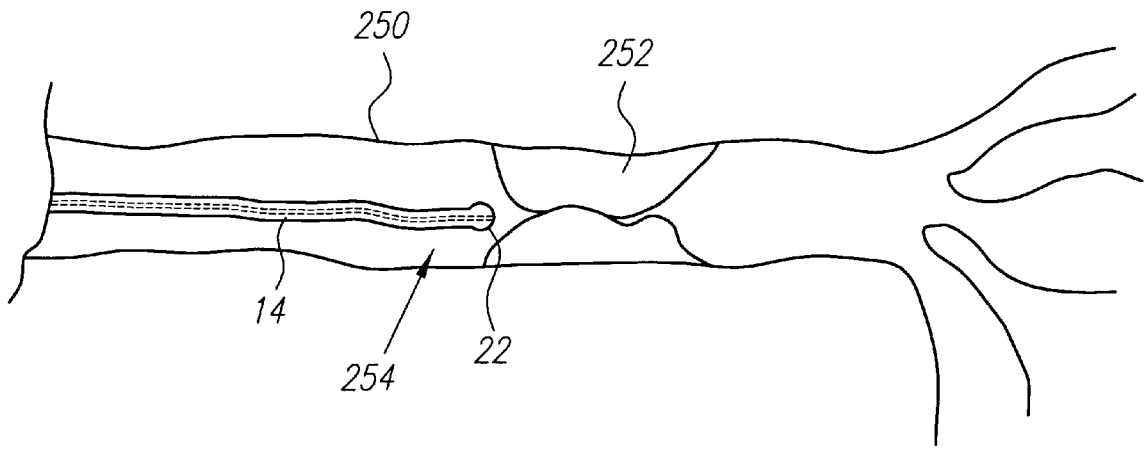
FIG. 13 is a partial side view of the rectilinear region of a blood vessel during operation of the vessel recanalization system, wherein the distal ablation tip is shown adjacent an occlusion within a rectilinear region of a blood vessel.

In preparation for the ablation procedure, the return electrode 72 is attached to the patient (not shown) using conductive jelly to ensure positive and dispersive electrical contact with the patient. Using known guide wire insertion techniques, typically using a guide sheath or steerable catheter, the guide wire 14 is routed through the vasculature until the distal ablation tip 22 is disposed just proximal to the total occlusion 252 of the blood vessel 250 (FIG. 13).

Figure 14:
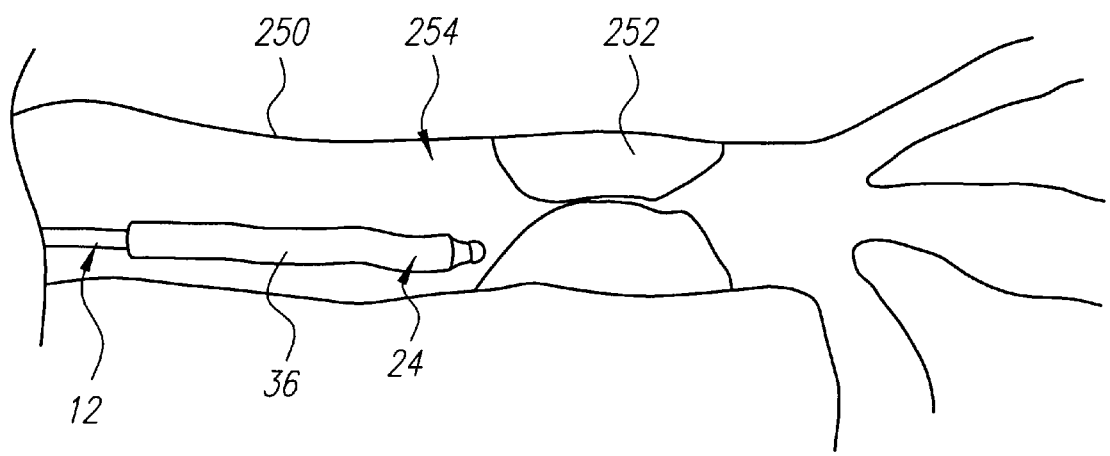
FIG. 14 is a partial side view of the blood vessel of FIG. 13, wherein the centering catheter is introduced over the ablative guide wire of FIG. 4.

With the centering mechanism 24 deactivated, i.e., the balloon 36 deflated, the centering catheter 12 is advanced over the guide wire 14 until the centering mechanism 24 is disposed adjacent the total occlusion 252 (FIG. 14). The centering mechanism 24 is positively prepared, i.e., inflation medium or contrast agent is conveyed via the preparation port 68 through the airless preparation lumen 44, into the balloon 36, out through the inflation lumen 42 and inflation port 66, thereby substantially removing all of the air from the balloon 36. In this manner, the radiopacity of the balloon 36 is improved. That is, air in the balloon 36 will not typically appear under standard fluoroscopy procedures, making the balloon 36 difficult to locate. Thus, removing air from the balloon 36 and completely filling the balloon 36 with contrast agent allows the balloon 36 to be more easily located.

Alternatively, the air can be removed from the balloon 36 by conveying the inflation medium or contrast agent into the inflation port 66 and out through the preparation port 68. It should be noted that rather than positively preparing the centering mechanism 24 while placed within the vasculature of the patient, it may be determined that it is preferable to positively prepare the centering mechanism 24 prior to placement within the vasculature of the patient. It should also be noted that the centering mechanism 24 can be positively prepared using means other than the combination of the airless preparation lumen 44 and inflation lumen 42.

Figure 15:
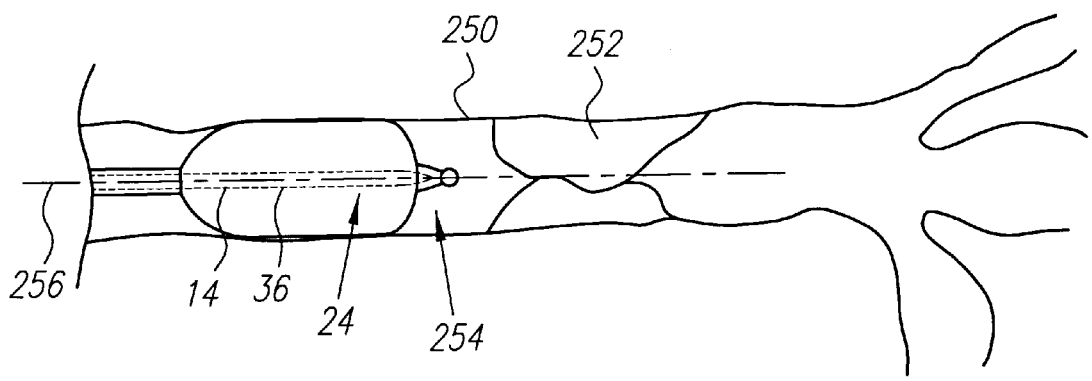
FIG. 15 is a partial side view of the blood vessel of FIG. 13, wherein the centering mechanism is activated to center the ablative guide wire within the blood vessel.
Figure 16:
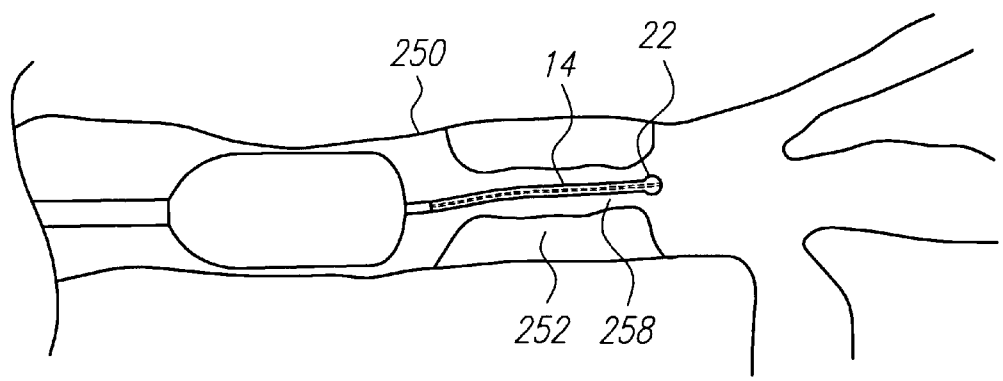
FIG. 16 is a partial side view of the blood vessel of FIG. 13, wherein the ablative guide wire of FIG. 15 has traversed the occlusion.

The centering mechanism 24 is then activated, i.e., the balloon 36 is inflated by sealing the preparation port 68 and conveying an inflation medium into the inflation port 66 of the adapter 32 until the balloon 36 expands into secure contact with the blood vessel 250 (FIG. 15). The sheath 46 is preferably manufactured, such that it collapses around the inner shaft 28 subsequent to sealing the preparation port 68.

As depicted, the centering mechanism 24 maintains the guide wire 14 along a centerline 256 of the blood vessel 250, such that the distal ablation tip 22 is substantially centered within the blood vessel 250 as it contacts the occlusion 252. The footswitch 74 shown in FIG. 1) is then depressed to energize the distal ablation tip 22. Moderate pressure is applied to the guide wire 14 in the distal direction to cause the distal ablation tip 22 to advance through the center of the occlusion 252 when RF energy is applied (FIG. 16) and creating a channel 258 within the center of the occlusion 252.

It should be noted that constant longitudinal movement of the distal ablation tip 22 should be exerted during delivery of the RF energy to the distal ablation tip 22 to prevent localized dehydration which would, in turn, cause high electrical resistivity, thus impeding further ablation. After the guide wire 14 has completely traversed the occlusion 252, the centering mechanism 24 is deactivated, i.e., the balloon 36 is deflated by opening the preparation port 68 and removing inflation medium from the inflation port 66.

Figure 17:
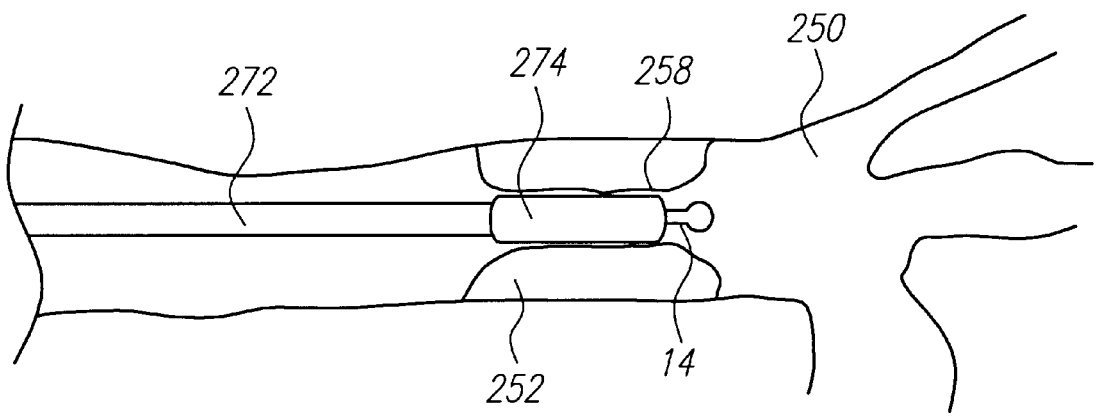
FIG. 17 is a partial side view of the blood vessel of FIG. 13, wherein a PTCA catheter is advanced over the ablative guide wire of FIG. 16.
Figure 18:
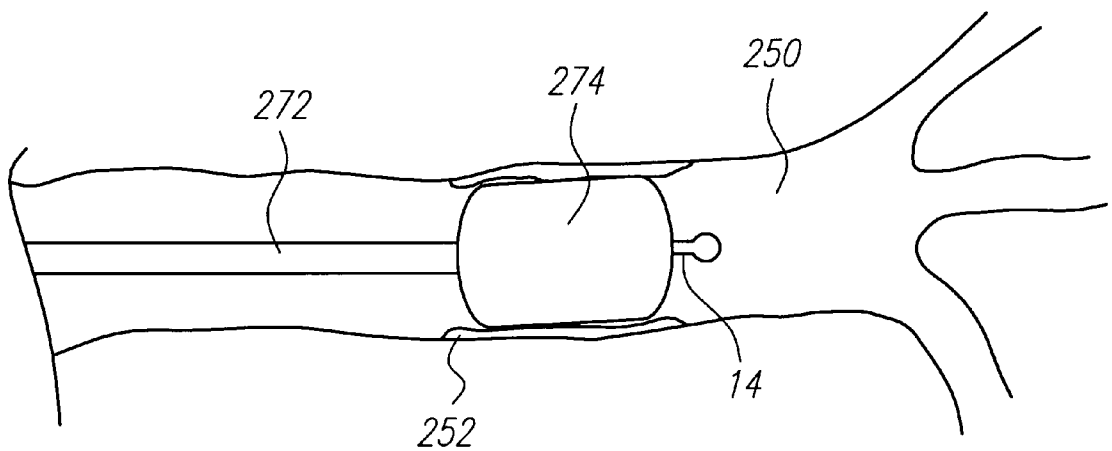
FIG. 18 is a partial side view of the blood vessel of FIG. 13, wherein the PTCA catheter of FIG. 17 is operated to dilate the blood vessel.

The centering catheter 12 is then removed, and the guide wire 14 is used to guide any of a variety of therapeutic devices for subsequent treatment of the occlusion or related disorders, including, but not limited to, PTCA, PTA or percutaneous transluminal rotary ablation catheters. For instance, a PTCA catheter 272, which employs a dilation balloon 274, can be introduced over the guide wire 14 and advanced until the dilation balloon 274 is disposed within the channel 258 of the occlusion B (FIG. 17). The dilation balloon B is then inflated to dilate the occlusion 252 (FIG. 18).

Figure 19:
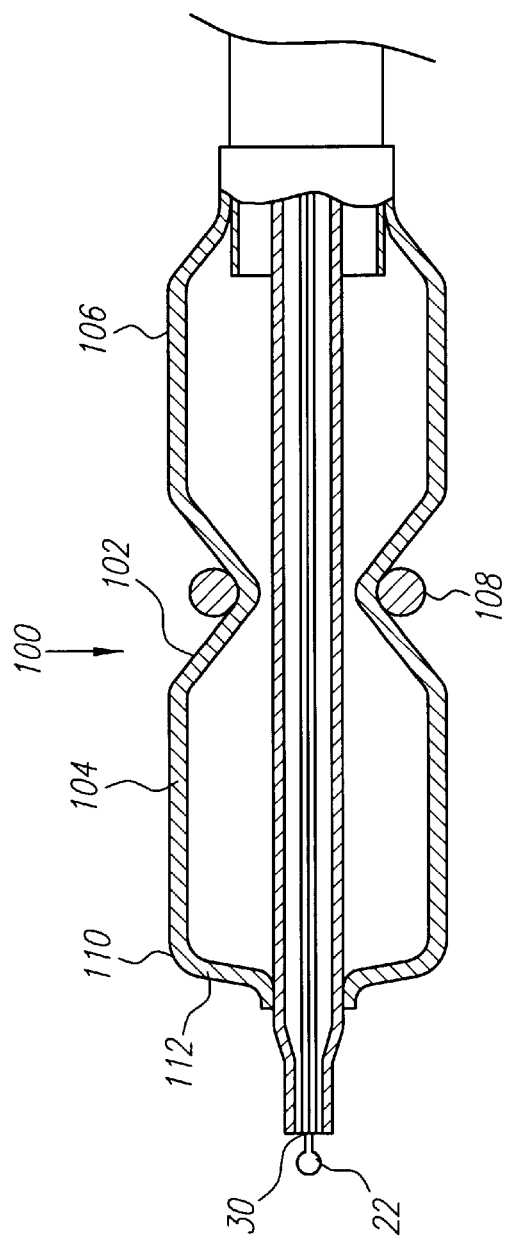
FIG. 19 is a cut away, partial side view of another centering catheter employed in the vessel recanalization system of FIG. 1, wherein the centering catheter particularly employs a segmented inflatable/deflatable balloon as a centering mechanism.

The centering catheter 12 can employ various other centering mechanisms to facilitate the therapy of totally occluded blood vessels. FIG. 19 depicts a centering mechanism 100, which provides a stable yet flexible platform, allowing the distal ablation tip 22 to be centered within a curvilinear region of a blood vessel.

The centering mechanism 100 particularly includes an inflatable/deflatable segmented balloon 102, which forms relatively short first and second segments 104 and 106 when inflated, preferably less than 8 mm. The segmented balloon 102 is composed of a material and is manufactured in a similar manner as that described above with respect to the balloon 36. The centering mechanism 100 further includes a restriction band 108, which is disposed around the segmented balloon 102 to create the respective segments 104 and 106 when inflated.

As with the balloon 36 of the centering mechanism 24, a distal side 110 of the first segment 104 includes a shoulder 112 with a substantially flat profile to ensure that the distal ablation tip 22 is centered as it exits the guide wire exit port 30.

The segmented balloon 102 provides both flexibility and stability to the distal end of the centering catheter 12, allowing the catheter body 18 to conform to a curvilinear region 262 of the blood vessel 250 (shown in FIG. 22) when the centering mechanism 100 is activated. Thus the centering mechanism 100 facilitates the centering of the distal ablation tip 22 within a curvilinear region 262, as well as the rectilinear region 254, of the blood vessel 250.

Flexibility of the centering catheter 12 is provided by the segmented nature of the centering mechanism 100 and the relative short longitudinal length of each of the segments 104 and 106, allowing the centering catheter 12 to be biased by the curvilinear geometry of the blood vessel 250 rather than by the centering mechanism 100. The gap between the respective segments 104 and 106 of the segmented balloon 102 can be varied to adjust the flexibility of the centering mechanism 100. Preferably, however, the gap is less then 4 mm to maintain stability along the length of the centering mechanism 100.

The overall longitudinal length of the centering mechanism 100 provides stability to the distal end of the centering catheter 12 in that it prevents the catheter body 18 from pitching, which would normally result from the use of a single short balloon in a curvilinear vessel. It should be noted that the segmented balloon 102 can comprise more than two segments to further enhance the stability of the centering mechanism 100.

Figure 20:
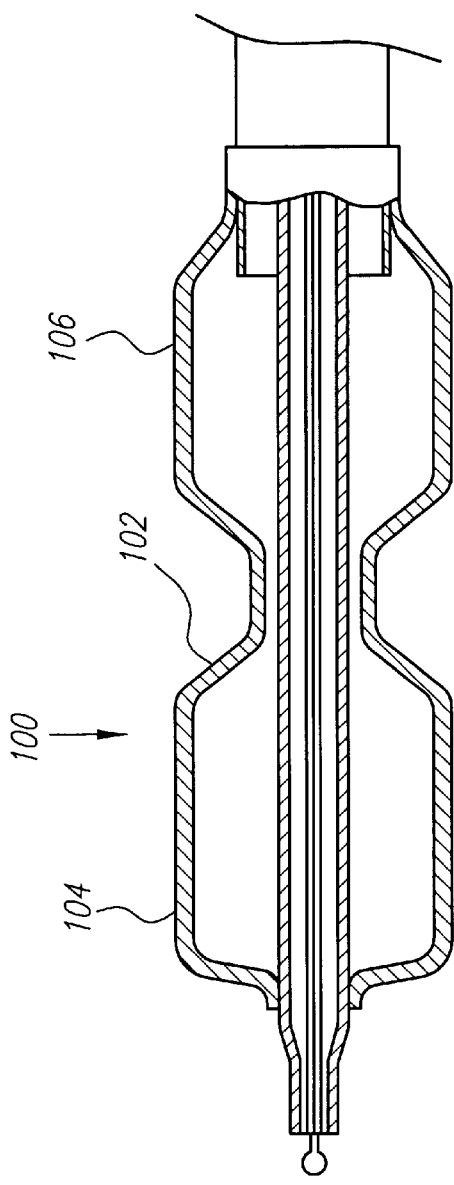
FIG. 20 is a cut away, partial side view of the centering catheter of FIG. 19, wherein the segmented inflatable/deflatable balloon comprises pre-formed segments.

In alternative embodiments, as depicted in FIG. 20, the segmented balloon 102 can be formed by stretching a single extruded piece of material over a shaped mandrel to create respective pre-formed segments 104 and 106. When inflated, the segmented balloon 102 naturally forms the respective segments 104 and 106, such that an external force, such as by restricting with bands, is not required.

Figure 21:
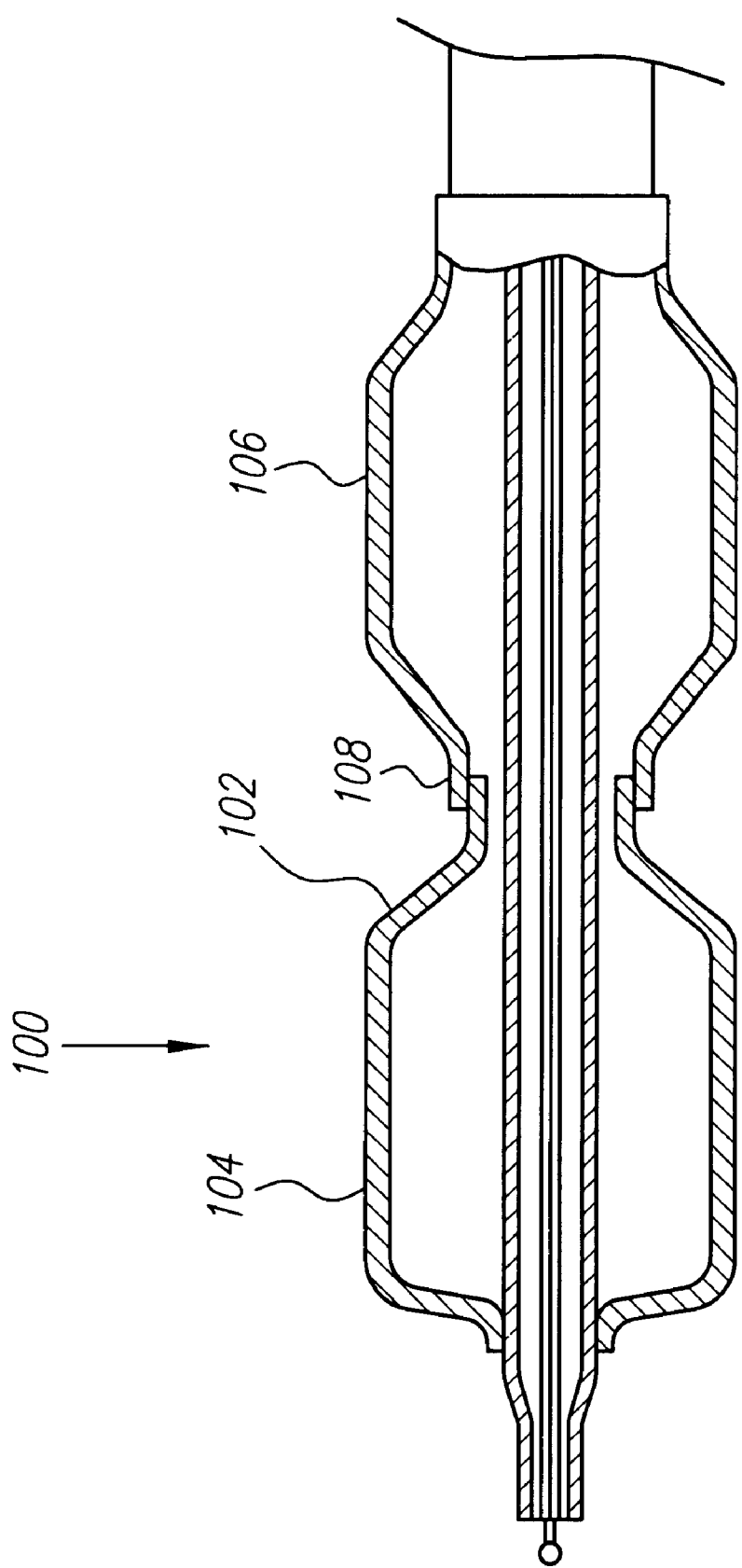
FIG. 21 is a cut away, partial side view of the centering catheter of FIG. 19, wherein the segmented inflatable/deflatable balloon comprises multiple pieces of material.

More alternatively, as shown in FIG. 21, an the segmented balloon 102 is composed of two pieces of extruded material, which are bonded to each other via a lap-joint 108 to form respective segments 104 and 106. Preferably, the total thickness of the material forming the lap-joint 108 is equal to the thickness of the material forming the remaining portions of the segmented balloon 102, such that the segmented balloon 102 has a uniform thickness.

When employing the centering mechanism 100, operation of the system 10 to recanalize an occlusion 260 within the curvilinear region 262 of the blood vessel 250 is similar to that described above with respect to the occlusion 252 within the rectilinear region 254 of the blood vessel 250.

Figure 22:
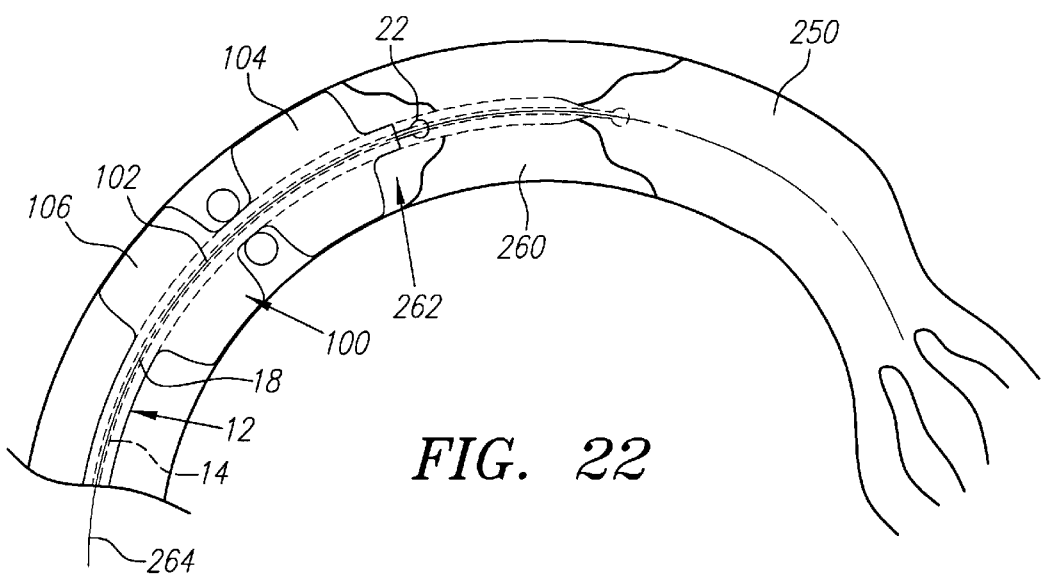
FIG. 22 is a partial side view of the curvilinear region of a blood vessel during operation of the vessel recanalization system of FIG. 1, wherein the centering mechanism is activated to center the ablative guide wire within the blood vessel.

As shown in FIG. 22, the flexibility and stability provided to the centering catheter 12 by the centering mechanism 100 when activated ensures that the guide wire 14 (shown in phantom) is maintained along the centerline 264 of the blood vessel 250, such that the distal ablation tip 22 is substantially centered within the blood vessel 250 as it contacts the occlusion 260.

Figure 23:
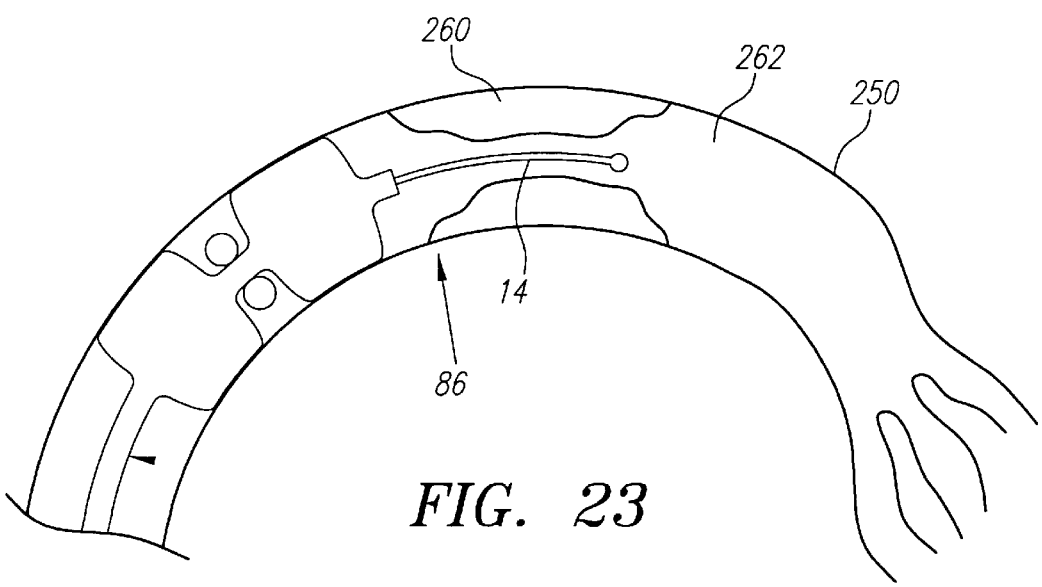
FIG. 23 is a partial side view of the curvilinear region of a blood vessel during operation of the vessel recanalization system of FIG. 1, wherein the occlusion is traversed by the ablative guide wire in a single ablation step.

As shown in FIG. 23, the distal end of the guide wire 14 is preformed to conform to the curvilinear geometry of the curvilinear region 262 of the blood vessel 250, such that the guide wire 14 is maintained along the centerline 264 of the blood vessel 250 as the guide wire 14 traverses the occlusion 260.

Figure 24:
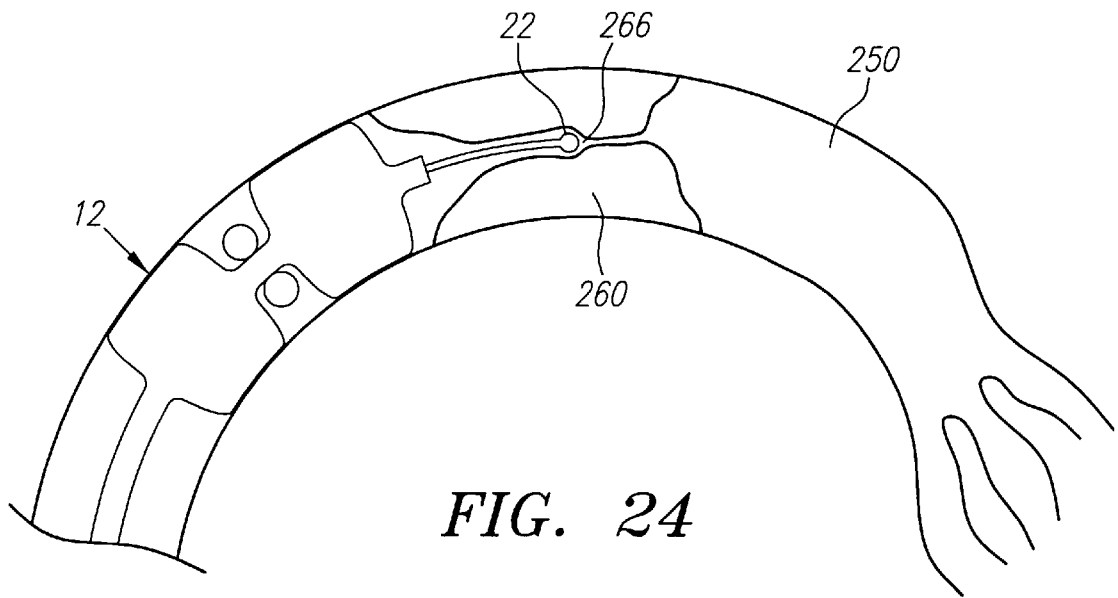
FIG. 24 is a partial side view of the curvilinear region of if a blood vessel during operation of the vessel recanalization system of FIG. 1, wherein the occlusion is partially traversed by the ablative guide wire.

Alternatively, rather than advancing the ablative guide wire through the occlusion 260 in a single ablation procedure and removing the occlusion 260 with a therapeutic device over a single therapeutic procedure, the occlusion 260 is traversed over a plurality of ablation procedures and removed over a plurality of therapeutic procedures. Towards this end, the generator 16 is activated and the distal ablation tip 22 is partially advanced through the occlusion 260 to create a partial channel 266 (FIG. 24)

Figure 25:
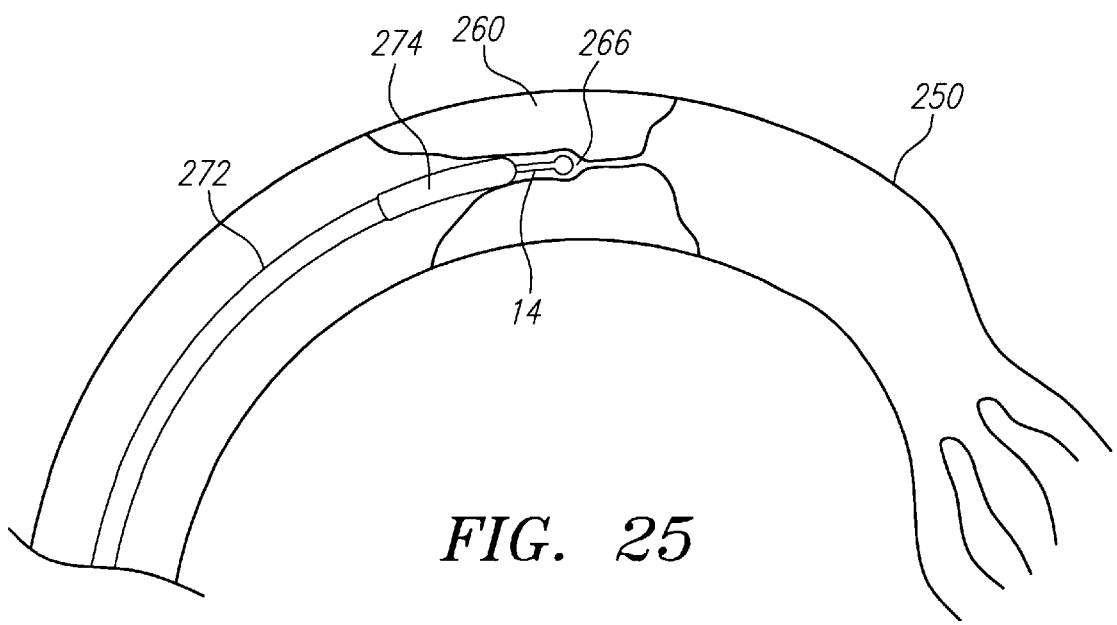
FIG. 25 is a partial side view of the blood vessel of FIG. 24, wherein a PTCA catheter is advanced over the ablative guide wire.
Figure 26:
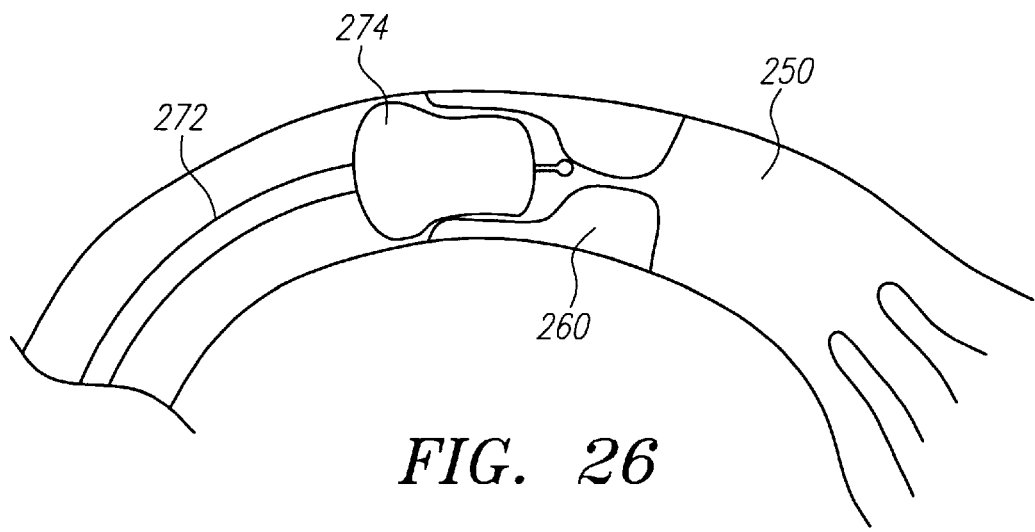
FIG. 26 is a partial side view of the blood vessel of FIG. 24, wherein the PTCA catheter of FIG. 25 is operated to partially dilate the blood vessel.
Figure 27:
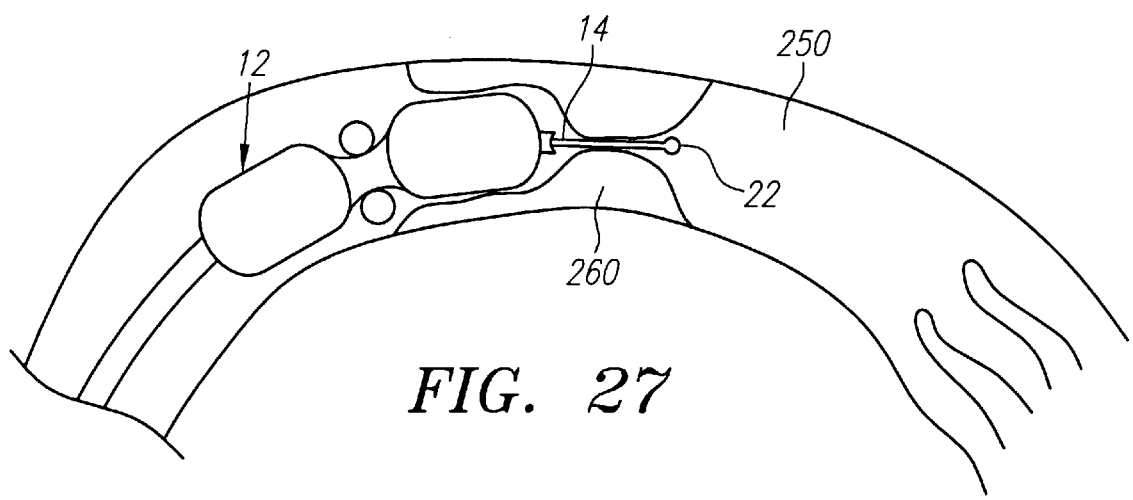
FIG. 27 is a partial side view of the blood vessel of FIG. 24, wherein the occlusion is totally traversed by the ablative guide wire.

The centering catheter 12 is removed and the therapeutic device, such as, e.g., the PTCA catheter 272 shown in FIGS. 17–18 is advanced up the guide wire 14 until the dilation balloon 274 is disposed within the partial channel 71 (Shown in FIG. 25). The dilation balloon 274 is inflated to dilate a portion of the occlusion 252 (Shown in FIG. 26). The PTCA catheter 272 is then removed and the centering catheter 12 is advanced up the guide wire 14 and the centering mechanism is activated (shown in Fig. 27). This process is repeated until the occlusion 260 has been totally recanalized and treated.

Figure 28:
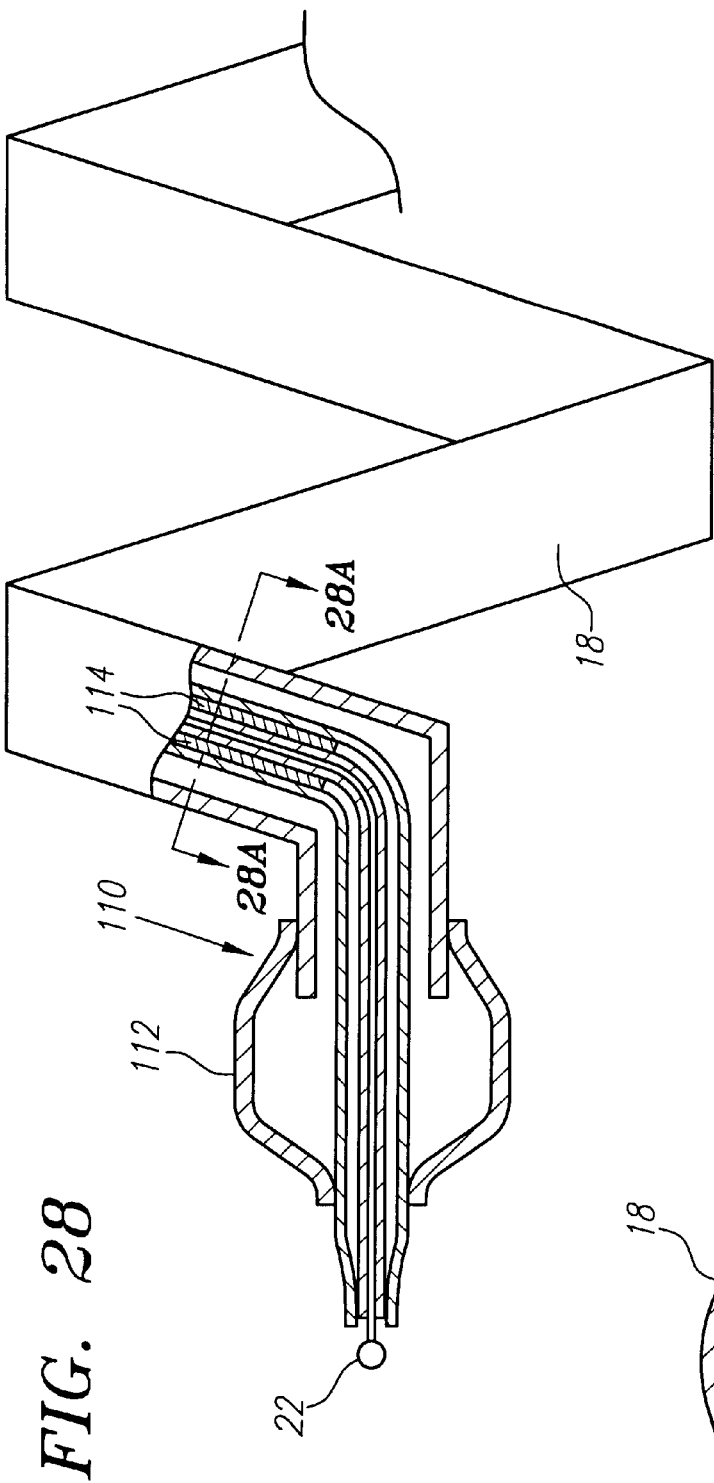
FIG. 28 is a cut away, partial side view of still another centering catheter employed in the vessel recanalization system of FIG. 1, wherein the centering catheter particularly employs a single inflatable/deflatable balloon and a plurality of resilient wires preshaped into a helix as a centering mechanism.
Figure 28A:
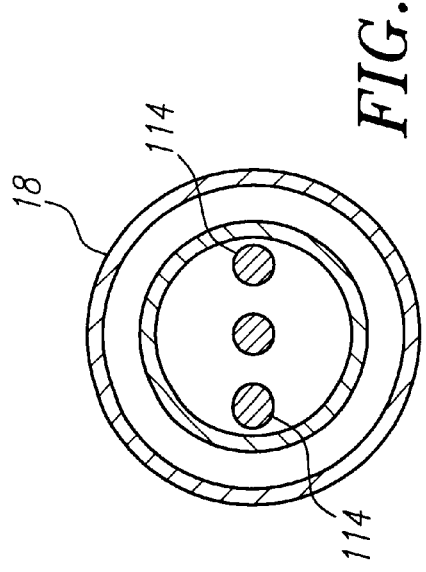
FIG. 28A is a cross-sectional view of the centering catheter of FIG. 28 taken along the line 28A—28A.

FIG. 28 depicts another centering mechanism 110, which allows the distal ablation tip 22 to be centered within the curvilinear region 262 of the blood vessel 250. The centering mechanism 110 particularly includes a relatively short inflatable/deflatable balloon 112 distally formed on the catheter body 18.

The balloon 112 is composed of a material and manufactured in a similar manner as that described above with respect to the balloon 36. The centering mechanism 110 further includes a resilient support 114 disposed in the catheter body 18 proximal to the balloon 112. The resilient support 114 is pre-formed into a complex geometry, and is composed of a resilient material, such as, e.g., Nickel Titanium, thereby imparting the same complex geometry onto the portion of the catheter body 18 in which it is disposed.

Figure 29:
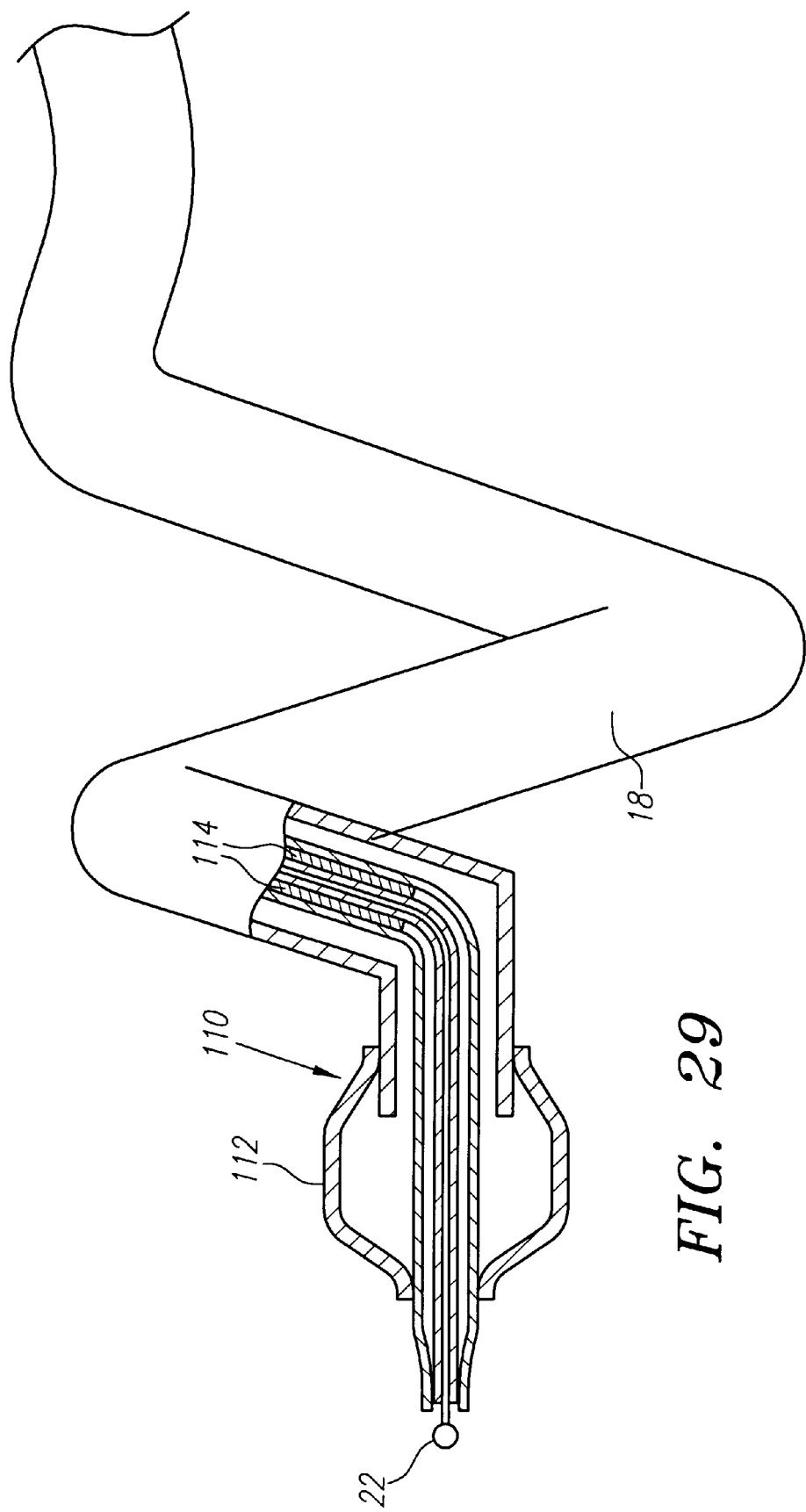
FIG. 29 is a cut away, partial side view of still another centering catheter employed in the vessel recanalization system of FIG. 1, wherein the centering catheter particularly employs a single inflatable/deflatable balloon and a plurality of resilient wires preshaped into a biplanar wave as a centering mechanism.

As depicted in FIG. 28, the complex geometry of the resilient support 114, and the portion of the catheter body 18 in which it is disposed, is helical. The resilient support 114 can be pre-formed into other complex geometries, however, such as, e.g., a bi-planar wave (i.e., the resilient support 114 includes alternating sections of waves that lie in orthogonal planes) as depicted in FIG. 29.

Figure 30:
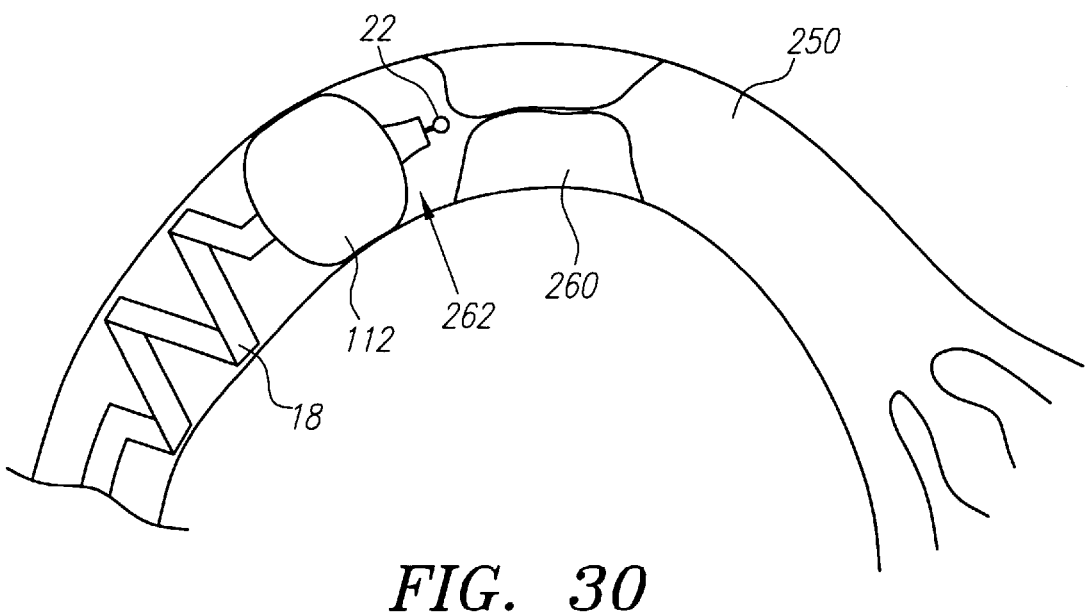
FIG. 30 is a partial side view of the centering catheter of FIG. 28, wherein the centering mechanism is activated to center an ablation tip of an ablative guide wire within a curvilinear region of the blood vessel.

The complex geometry allows the portion of the catheter body 18 proximal to the balloon 112 to conform to the vessel 250. In this manner, as depicted in FIG. 30, both flexibility and stability is provided to the centering catheter 12, thereby facilitating proper centering of the distal ablation tip 22 within the curvilinear region 262 of the blood vessel 250 as the distal ablation tip 12 traverses the total occlusion 260.

Figure 31:
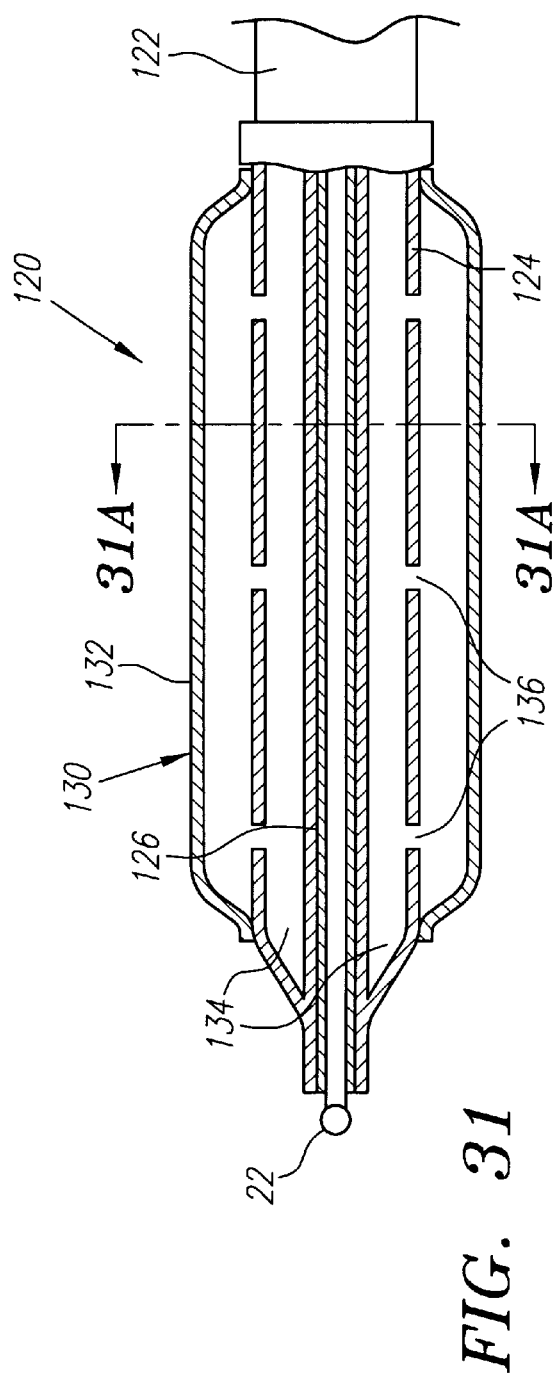
FIG. 31 is a cut away, partial side view of still another centering catheter employed in the vessel recanalization system of FIG. 1, wherein the centering catheter particularly employs a single inflatable/deflatable balloon as a centering mechanism and a catheter body with coextruded inflation and guide wire lumens.
Figure 31A:
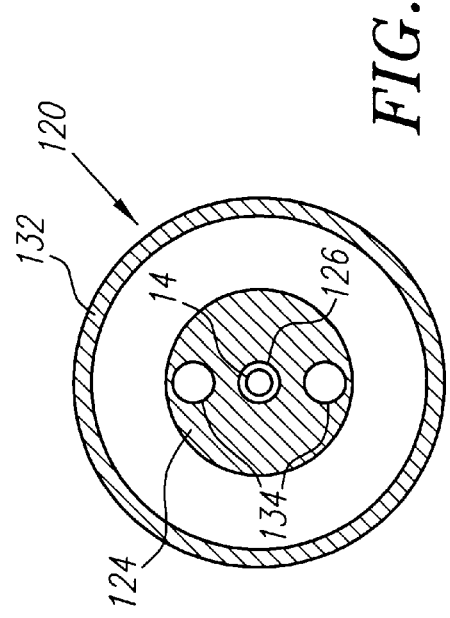
FIG. 31A is a cross-sectional view of the centering catheter of FIG. 31 taken along the line 31A—31A.

FIG. 31 depicts an alternative preferred embodiment of a centering catheter 120, which can be employed in the vessel recanalization system 10. The centering catheter 120 includes a catheter body 122 with co-extruded lumens. In particular, the catheter body 122 includes a flexible elongate tubular member 124 in which there is extruded a guide wire lumen 126 for disposition of the guide wire 14.

The centering catheter 120 further includes a centering mechanism 130, which facilitates the centering of the distal ablation tip 22 within the totally occluded rectilinear vessel 250 (shown in FIG. 13). The centering mechanism 130 comprises an inflatable/deflatable balloon 132, much like the balloon 36 described above. The balloon 132 is secured to the distal end of the tubular member 124.

The centering catheter 120 further includes inflation lumens 134, which are co-extruded with the guide wire lumen 126 in the tubular member 124, and inflation ports 136, which traverse the wall of the tubular member 124 to provide fluid communication between the inflation lumens 134 and the balloon 132. Operation of the centering catheter 120 is similar to that of the centering catheter 12 described above.

Figure 32:
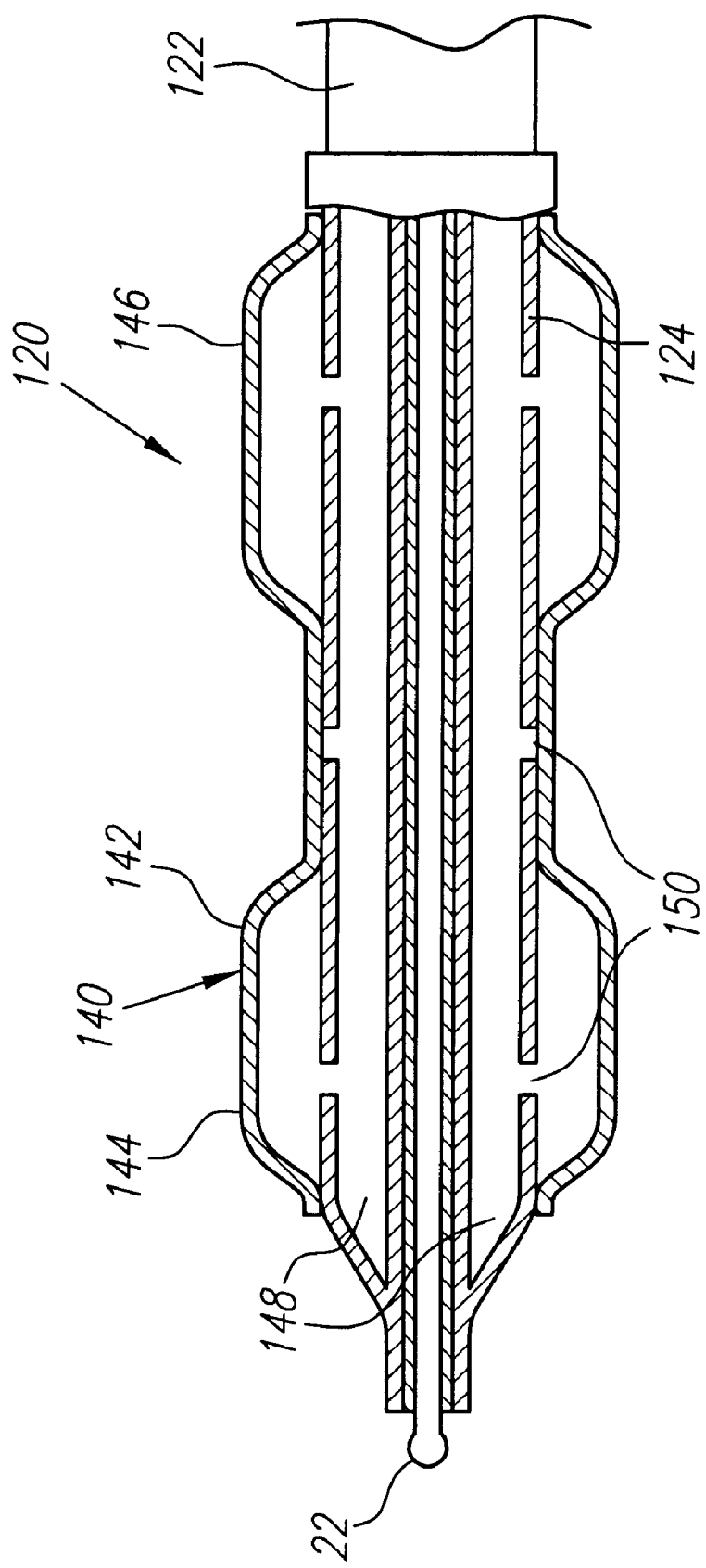
FIG. 32 is a cut away, partial side view of still another centering catheter employed in the vessel recanalization system of FIG. 1, wherein the centering catheter particularly employs a segmented inflatable/deflatable balloon as a centering mechanism and a catheter body with coextruded inflation and guide wire lumens.

The centering catheter 120 can employ various other centering mechanisms to facilitate the therapy of totally occluded blood vessels. FIG. 32 depicts a centering mechanism 140 that can be employed by the centering catheter 120 to facilitate the centering of the distal ablation tip 22 within the curvilinear region 262 of the blood vessel 250 (shown in FIG. 22).

In particular, the centering mechanism 140 comprises a segmented inflatable/deflatable balloon 142 with respective segments 144 and 146, much like the balloon 102 described above. Like the centering mechanism 130 described above, the balloon 142 is secured to the distal end of the tubular member 124. The centering catheter 120 further includes inflation lumens 148, which are co-extruded with the guide wire lumen 126 in the tubular member 124, and inflation ports 150, which traverse the wall of the tubular member 124 to provide fluid communication between the inflation lumens 148 and the balloon 142. Operation of the centering catheter 120 is similar to that of the centering catheter 12 described above.

FIG. 33 depicts a centering mechanism 160 that can be employed by the centering catheter 120 to facilitate the centering of the distal ablation tip 22 within the curvilinear region 262 of the blood vessel 250 (shown in FIG. 22).

In particular, the centering mechanism 160 comprises a pair of pre-shaped wires 162, each of which includes a wire shaft 164 and a distally located centering ring 166. The centering rings 166 are composed of a pre-shaped material, such as, e.g., Nickel Titanium. In this manner, the centering rings 166 form circular rings, which are orthogonal to the shafts of the wires, in the absence of external force.

The centering catheter 120 further includes a pair of pull wire lumens 168, which are co-extruded with the guide wire lumen 126 in the tubular member 124. The pair of pre-shaped wires 162 are slidingly disposed within the respective pull wire lumens 168. The pull wire lumens 168 distally terminate into respective pull wire exit ports 170.

Figure 34:
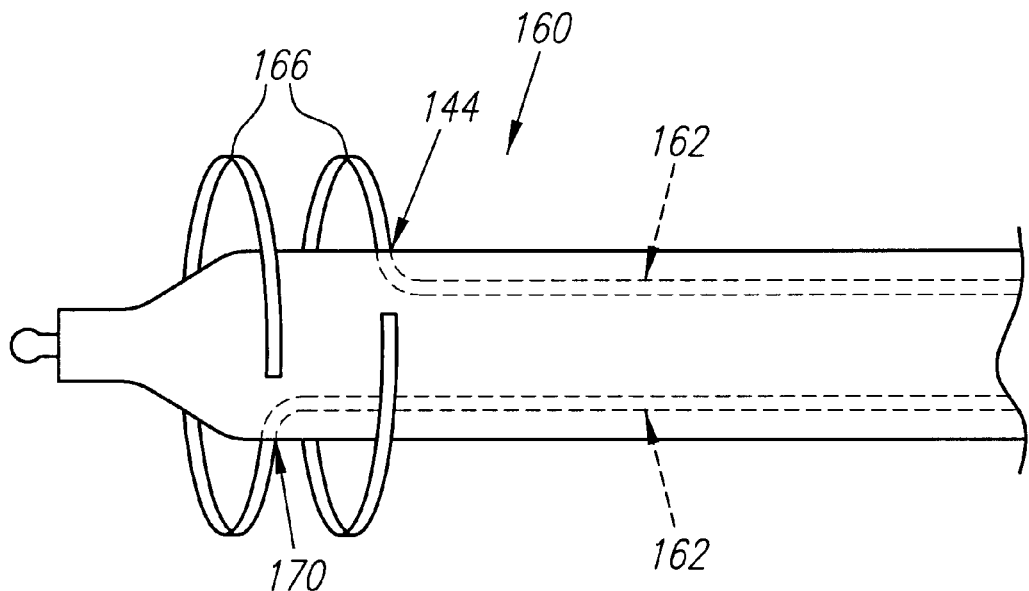
FIG. 34 is a partial side view of the centering catheter of FIG. 33, wherein the centering rings are deployed.

As depicted in FIG. 34, distal longitudinal displacement of the pre-shaped wires 162 through the respective wire lumens 168 causes the distal ends of the pre-shaped wires 162 (shown partially in phantom) to extend out the respective pull wire exit ports 170, allowing the centering rings 166 to expand into their pre-shaped form, thereby activating the centering mechanism 160.

Figure 35:
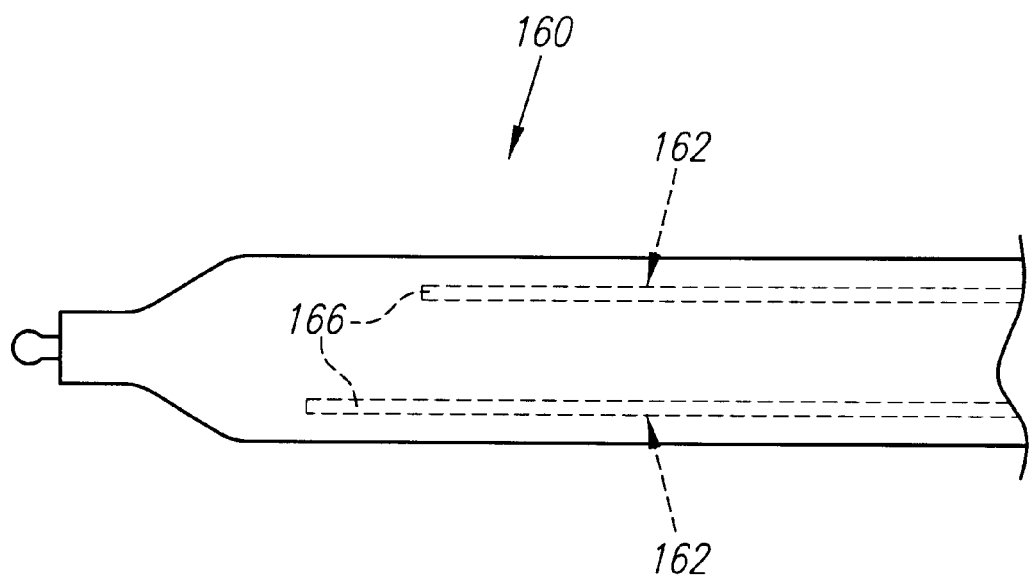
FIG. 35 is a partial side view of the centering catheter of FIG. 33, wherein the centering rings are retracted.

Contrariwise, as depicted in FIG. 35, proximal longitudinal displacement of the pre-shaped wires 162 through the respective wire lumens 168 causes the distal ends of the pre-shaped wires 162 (shown in phantom) to retract into the respective pull wire exit ports 170, storing the centering rings 166 within the respective wire lumens 168 and deactivating the centering mechanism 160.

It should be noted that more than two pre-shaped wires 162 and pull wire lumens 168 can be employed in the centering mechanism 160 to provide further stability to the centering catheter 120.

While preferred methods and embodiments have been shown and described, it will be apparent to one of ordinary skill in the art that numerous alterations may be made without departing from the spirit or scope of the invention. Therefore, the invention is not to be limited except in accordance with the following claims.

What is claimed:

1. A method for recanalization of a blood vessel, comprising:

positioning a conductive guide wire having a distal end ablation tip into a blood vessel, such that the ablation tip is adjacent an occlusion to be traversed;

centering the guide wire ablation tip within the blood vessel by employing an operable centering mechanism located on a distal end of a centering catheter;

conveying radio frequency (RF) RF energy through the guide wire to the distal ablation tip; and advancing the energized ablation tip through the occlusion, wherein the guide wire ablation tip is centered by advancing said centering catheter over the guide wire until said centering mechanism is adjacent the occlusion, and then activating the centering mechanism to thereby center the guide wire ablation tip within the blood vessel and to maintain the guide wire ablation tip in said centered position throughout said recanalization procedure.

2. The method of claim 1, wherein the occlusion lies in a curvilinear region of the blood vessel lumen, and the centering catheter conforms to the curvilinear region.

3. The method of claim 1, further comprising removing the centering catheter from the guide wire;

advancing a therapeutic device over the guide wire until the device is positioned proximate the occlusion, and operating the therapeutic device.

4. The method of claim 3, wherein the therapeutic device is an atheroectomy catheter.

5. The method of claim 3, wherein the therapeutic device is an angioplasty catheter.

6. The method of claim 3, wherein the occlusion lies in a curvilinear region of the blood vessel, advancement of the ablative guide wire through the occlusion is accomplished via a plurality of ablation procedures, and treatment of the occlusion performed via a plurality of therapeutic procedures.

7. An ablative guide wire assembly for use in intravascular medical procedures comprising an elongate conductive guide wire having a distal end and an ablative tip formed on the guide wire distal end, the ablation tip having a generally non-traumatic structure with a discontinuous feature, wherein the non-traumatic structure is spherically shaped, and wherein the discontinuous feature comprises a tapered protrusion disposed on a distal facing surface of the structure.

* * * * *

UNITED STATES PATENT AND TRADEMARK OFFICE
CERTIFICATE OF CORRECTION

PATENT NO.     : 6,210,408 B1
DATED          : April 3, 2001
INVENTOR(S)    : Verivada Chandrasekaran et al.

It is certified that error appears in the above-identified patent and that said Letters Patent is hereby corrected as shown below:

<u>Title page,</u>
Item [56], delete "0 688 580 A1   6/1994(EP) ....A61N/5/10"

<u>Column 10,</u>
Line 27, delete "latinum" and insert -- platinum --.
Line 28, delete "paqueness" and insert -- opaqueness --.

<u>Column 12,</u>
Line 36, delete "/V/$_{tissue}$ = V$_{source}$ (Z$_{tissue}$ /(Z$_{tissue}$ + Z$_C$)" and insert -- /V/$_{tissue}$ $\cong$ V$_{source}$ (Z$_{tissue}$/(Z$_{tissue}$ + Z$_C$)) --.

Signed and Sealed this

Eighteenth Day of March, 2003

JAMES E. ROGAN
*Director of the United States Patent and Trademark Office*